(12) United States Patent
Nagorsen

US010191034B2

(10) Patent No.: US 10,191,034 B2
(45) Date of Patent: Jan. 29, 2019

(54) DOSAGE REGIMEN FOR ADMINISTRATING A CD19×CD3 BISPECIFIC ANTIBODY TO PATIENTS AT RISK FOR POTENTIAL ADVERSE EFFECTS

(75) Inventor: Dirk Nagorsen, Munich (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 0 days.

(21) Appl. No.: 14/113,755

(22) PCT Filed: Apr. 30, 2012

(86) PCT No.: PCT/EP2012/001857
§ 371 (c)(1),
(2), (4) Date: Feb. 11, 2014

(87) PCT Pub. No.: WO2012/146394
PCT Pub. Date: Nov. 1, 2012

(65) Prior Publication Data
US 2014/0199307 A1 Jul. 17, 2014

Related U.S. Application Data

(60) Provisional application No. 61/479,961, filed on Apr. 28, 2011.

(51) Int. Cl.
*G01N 33/50* (2006.01)
*C07K 16/28* (2006.01)
*A61K 39/00* (2006.01)

(52) U.S. Cl.
CPC ..... *G01N 33/5094* (2013.01); *C07K 16/2803* (2013.01); *C07K 16/2809* (2013.01); *A61K 2039/505* (2013.01); *A61K 2039/507* (2013.01); *C07K 2317/31* (2013.01); *C07K 2317/622* (2013.01)

(58) Field of Classification Search
CPC ........ A61K 2039/545; A61K 2039/507; A61K 2039/505; A61K 39/395; A61K 39/39558; C07K 16/2809; C07K 16/2803; C07K 2317/31
See application file for complete search history.

(56) References Cited

U.S. PATENT DOCUMENTS 8,840,888 B2 * 9/2014 Nagorsen et al. ......... 424/136.1
2015/0071928 A1 * 3/2015 Nagorsen et al. ......... 424/136.1

FOREIGN PATENT DOCUMENTS

| CN | 102711822 A | 10/2012 |
|---|---|---|
| EP | 623679 A1 | 11/1994 |
| WO | WO-199954440 A1 | 10/1999 |
| WO | WO-2004/106381 A1 | 12/2004 |
| WO | WO-2007/068354 A1 | 6/2007 |
| WO | WO-2008/119565 A2 | 10/2008 |
| WO | WO-2008/119567 A2 | 10/2008 |
| WO | WO-2011/051307 A1 | 5/2011 |

OTHER PUBLICATIONS

Viardot et al., Abstract #2880, ASH Annual Meeting, Blood, Dec. 7, 2010; 116:1186-87.*
Mølhøj et al., Mol. Immunol. 2007; 44:1935-43.*
Schlereth et al., Cancer Immunol Immunother 2006; 55:503-14.*
Bargou et al., Science 2008; 321:974-97.*
Chames & Baty, mAbs 2009; 1(6):539-47.*
Almagro & Fransson, Frontiers in Bioscience 2008; 13:1619-33.*
Rudikoff et al., Proc. Nat'l Acad. Sci. USA 1982; 79:1979-83.*
Brown et al., J. Immunol. 1996; 156(9):3285-91.*
Bargou et al., Tumor regression in cancer patients by very low doses of a T cell-engaging antibody, *Science* 321 :974-7 (2008).
Crick, Codon—anticodon pairing: The wobble hypothesis, *J. Mol. Biol.* 19:548-55 (1966).
DuBois, Clinical Calorimetry, *Arch. Int. Med.* 17:863-871 (1916).
Gehan, Estimation of human body surface area from height and weight, *Cancer Chemother. Rep.* 54:225-35 (1970).
GenBank Accession No. AAA69966, CD19 [*Homo sapiens*], dated Jul. 18, 1995.
GenBank Accession No. NM_000733, *Homo sapiens* CD3e molecule, epsilon (CD3-TCR complex) (CD3E), mRNA, dated Mar. 24, 1999.
Gobeler et al., Blinatumomab (CD3/CD19 Bite antibody) results in a high response rate in patients with relapsed non-Hodgkin lymphoma (NHL) including MCL and DLBCL, retrieved from www.micromet.com/assets/fnmicrometicml-nhl-oral-15june.aspx on Jan. 18,2<www.micromet.com/assets/fnmicrometicml-nhl-oral-15june.aspx%20on%20January%2018,2> 2012.
Goebeler et al., CD3/CD19 Bispecific bite (R) antibody blinatumomab treatment of non-Hodgkin lymphoma (NHL) patients: 60 µg/m²/D by continuous infusion is tolerable and resulting in durable response, *Haematologica* 95:23 (2010).
Haycock, Geometric method for measuring body surface area: a height-weight formula validated in infants, children, and adults, *J Pediatrics* 93:1:62-6 (1978).
International Preliminary Report on Patentability, PCT/EP2012/001857, dated Oct. 29, 2013.
International Search Report and Written Opinion of the International Searching Authority, European Patent Office, PCT/EP2012/001857, dated Aug. 20, 2012.
Kabat et al., Sequences of Proteins of Immunological Interest, (5th ed.) U.S. Department of Health and Human Services (1991).

(Continued)

*Primary Examiner* — Jessica H Roark
(74) *Attorney, Agent, or Firm* — Marshall, Gerstein & Borun LLP

(57) ABSTRACT

A method for assessing the risk of potential adverse effects for a human patient receiving a CD19×CD3 bispecific antibody is provided. The method comprises determining the total B count in the patient, and identifying a B cell number indicative of a patient at risk of potential adverse effects from the antibody. The method further provides a dosing schedule for administering the antibody to the patient identified as at risk of potential adverse effects. Also provided is a pharmaceutical package or kit comprising a first dose and a second dose, and optionally a third dose, of the CD19×CD3 bispecific antibody as defined in the methods/dosage regimen of the disclosure.

Figure 2:
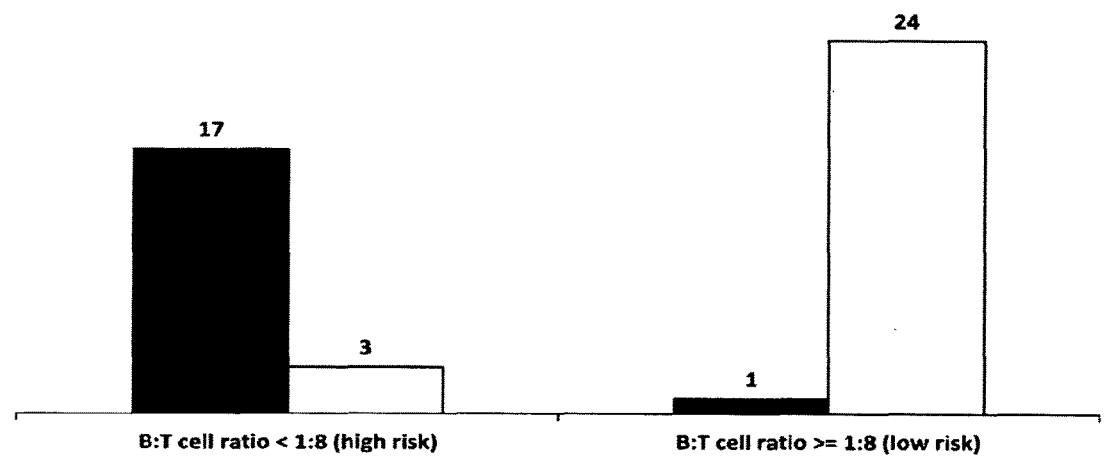
Figure 2:
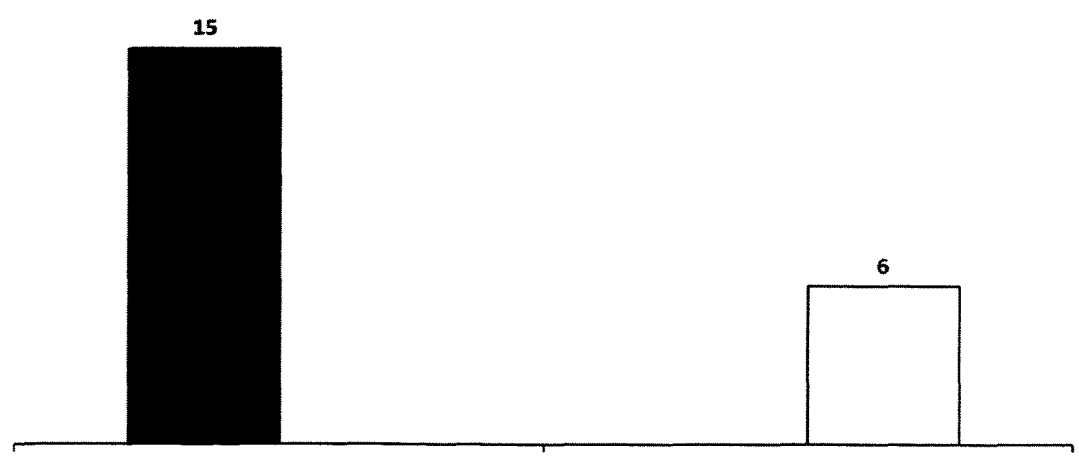

20 Claims, 2 Drawing Sheets
Specification includes a Sequence Listing.

(56) References Cited

OTHER PUBLICATIONS

Leandro et al., Reconstitution of peripheral blood B cells after depletion with rituximab in patients with rheumatoid arthritis, *Arthritis Rheum.* 54(2):613-20 (2006).
Mosteller, Simplified calculation of body-surface area, *N. Engl. J. Med.* 317(17):1098 (1987).
Needleman et al., A general method applicable to the search for similarities in the amino acid sequence of two proteins, *J. Mol. Biol.* 48:443-53 (1970).
Smith et al., Comparison of Biosequences, *Adv. Appl. Math.* 2:482-9 (1981).
Viardot et al., Treatment of patients with non-Hodgkin lymphoma (NHL) with CD19/CD3 bispectific antibody blinatumomab (MT103): Double-step dose increase to continuous infusion of 60 µg/m$^2$/d is tolerable and highly effective, *ASH Annual Meeting Abs.* 116:2880 (2010).
Matthias Klinger, [Mode of Action of the Bispecific Anti-CD19 x Anti-CD3 BiTE Antibody MT103 in Patients with Relapsed Indolent B-cell non-Hodgkin Lymphoma], Dissertation, Eberhard Karls University, Tuebingen, Germany, dated Jan. 1, 2009. English translation (pp. 1-107) of German dissertation (pp. 108-221).

* cited by examiner

Figure 1

|  | B cell cut-off 42.5/μL (median) | | B cell cut-off 35/μL | | B cell cut-off 50/μL | |
|---|---|---|---|---|---|---|
|  | < | > | < | > | < | > |
| CNS + | 16 | 3 | 16 | 3 | 16 | 3 |
| CNS - | 28 | 41 | 24 | 46 | 29 | 41 |
| Total | 44 | 44 | 40 | 49 | 45 | 44 |
| CNS + [%] | 36.4 | 6.8 | 35.5 | 6.1 | 40.0 | 6.7 |

SEQUENCE LISTING

```
<160> NUMBER OF SEQ ID NOS: 23

<210> SEQ ID NO 1
<211> LENGTH: 498
<212> TYPE: PRT
<213> ORGANISM: Artificial Sequence
<220> FEATURE:
<223> OTHER INFORMATION: CD19xCD3 bispecific single chain antibody

<400> SEQUENCE: 1

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys Gly
            100                 105                 110

Gly Gly Gly Ser Gly Gly Gly Gly Ser Gly Gly Gly Gly Ser Gln Val
        115                 120                 125

Gln Leu Gln Gln Ser Gly Ala Glu Leu Val Arg Pro Gly Ser Ser Val
    130                 135                 140

Lys Ile Ser Cys Lys Ala Ser Gly Tyr Ala Phe Ser Ser Tyr Trp Met
145                 150                 155                 160
```

Asn Trp Val Lys Gln Arg Pro Gly Gln Gly Leu Glu Trp Ile Gly Gln
            165                 170                 175

Ile Trp Pro Gly Asp Gly Asp Thr Asn Tyr Asn Gly Lys Phe Lys Gly
        180                 185                 190

Lys Ala Thr Leu Thr Ala Asp Glu Ser Ser Ser Thr Ala Tyr Met Gln
        195                 200                 205

Leu Ser Ser Leu Ala Ser Glu Asp Ser Ala Val Tyr Phe Cys Ala Arg
    210                 215                 220

Arg Glu Thr Thr Thr Val Gly Arg Tyr Tyr Ala Met Asp Tyr Trp
225                 230                 235                 240

Gly Gln Gly Thr Thr Val Thr Val Ser Ser Gly Gly Gly Ser Asp
            245                 250                 255

Ile Lys Leu Gln Gln Ser Gly Ala Glu Leu Ala Arg Pro Gly Ala Ser
        260                 265                 270

Val Lys Met Ser Cys Lys Thr Ser Gly Tyr Thr Phe Thr Arg Tyr Thr
        275                 280                 285

Met His Trp Val Lys Gln Arg Pro Gly Gln Gly Leu Glu Trp Ile Gly
    290                 295                 300

Tyr Ile Asn Pro Ser Arg Gly Tyr Thr Asn Tyr Asn Gln Lys Phe Lys
305                 310                 315                 320

Asp Lys Ala Thr Leu Thr Thr Asp Lys Ser Ser Ser Thr Ala Tyr Met
            325                 330                 335

Gln Leu Ser Ser Leu Thr Ser Glu Asp Ser Ala Val Tyr Tyr Cys Ala
        340                 345                 350

Arg Tyr Tyr Asp Asp His Tyr Cys Leu Asp Tyr Trp Gly Gln Gly Thr
        355                 360                 365

Thr Leu Thr Val Ser Ser Val Glu Gly Gly Ser Gly Gly Ser Gly Gly
    370                 375                 380

Ser Gly Gly Ser Gly Gly Val Asp Asp Ile Gln Leu Thr Gln Ser Pro
385                 390                 395                 400

Ala Ile Met Ser Ala Ser Pro Gly Glu Lys Val Thr Met Thr Cys Arg
            405                 410                 415

Ala Ser Ser Ser Val Ser Tyr Met Asn Trp Tyr Gln Gln Lys Ser Gly
        420                 425                 430

Thr Ser Pro Lys Arg Trp Ile Tyr Asp Thr Ser Lys Val Ala Ser Gly
        435                 440                 445

Val Pro Tyr Arg Phe Ser Gly Ser Gly Ser Gly Thr Ser Tyr Ser Leu
    450                 455                 460

Thr Ile Ser Ser Met Glu Ala Glu Asp Ala Ala Thr Tyr Tyr Cys Gln
465                 470                 475                 480

Gln Trp Ser Ser Asn Pro Leu Thr Phe Gly Ala Gly Thr Lys Leu Glu
            485                 490                 495

Leu Lys

<210> SEQ ID NO 2
<211> LENGTH: 1494
<212> TYPE: DNA
<213> ORGANISM: Artificial Sequence
<220> FEATURE:
<223> OTHER INFORMATION: CD19xCD3 bispecific single chain antibody

<400> SEQUENCE: 2
gatatccagc tgacccagtc tccagcttct ttggctgtgt ctctagggca gagggccacc      60
atctcctgca aggccagcca agtgttgat tatgatggtg atagttattt gaactggtac     120

```
caacagattc caggacagcc acccaaactc ctcatctatg atgcatccaa tctagtttct    180
gggatcccac ccaggtttag tggcagtggg tctgggacag acttcaccct caacatccat    240
cctgtggaga aggtggatgc tgcaacctat cactgtcagc aaagtactga ggatccgtgg    300
acgttcggtg gagggaccaa gctcgagatc aaaggtggtg gtggttctgg cggcggcggc    360
tccggtggtg gtggttctca ggtgcagctg cagcagtctg ggctgagct ggtgaggcct     420 gggtcctcag tgaagatttc ctgcaaggct tctggctatg cattcagtag ctactggatg    480
aactgggtga agcagaggcc tggacaggt cttgagtgga ttggacagat ttggcctgga     540
gatggtgata ctaactacaa tggaaagttc aagggtaaag ccactctgac tgcagacgaa    600
tcctccagca cagcctacat gcaactcagc agcctagcat ctgaggactc tgcggtctat    660
ttctgtgcaa gacgggagac tacgacggta ggccgttatt actatgctat ggactactgg    720
ggccaaggga ccacggtcac cgtctcctcc ggaggtggtg gatccgatat caaactgcag    780
cagtcagggg ctgaactggc aagacctggg gcctcagtga agatgtcctg caagacttct    840
ggctacacct ttactaggta cacgatgcac tgggtaaaac agaggcctgg acagggtctg    900
gaatggattg gatacattaa tcctagccgt ggttatacta attacaatca gaagttcaag    960
gacaaggcca cattgactac agacaaatcc tccagcacag cctacatgca actgagcagc   1020
ctgacatctg aggactctgc agtctattac tgtgcaagat attatgatga tcattactgc   1080
cttgactact ggggccaagg caccactctc acagtctcct cagtcgaagg tggaagtgga   1140
ggttctggtg aagtggagg ttcaggtgga gtcgacgaca ttcagctgac ccagtctcca    1200
gcaatcatgt ctgcatctcc aggggagaag gtcaccatga cctgcagagc cagttcaagt   1260
gtaagttaca tgaactggta ccagcagaag tcaggcacct cccccaaaag atggatttat   1320
gacacatcca agtggcttc tggagtccct tatcgcttca gtggcagtgg gtctgggacc    1380
tcatactctc tcacaatcag cagcatggag gctgaagatg ctgccactta ttactgccaa   1440
cagtggagta gtaacccgct cacgttcggt gctgggacca gctggagct gaaa          1494
```

<210> SEQ ID NO 3
<211> LENGTH: 124
<212> TYPE: PRT
<213> ORGANISM: Artificial Sequence
<220> FEATURE:
<223> OTHER INFORMATION: VH anti CD19

<400> SEQUENCE: 3

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120
```

```
<210> SEQ ID NO 4
<211> LENGTH: 372
<212> TYPE: DNA
<213> ORGANISM: Artificial Sequence
<220> FEATURE:
<223> OTHER INFORMATION: VH anti CD19

<400> SEQUENCE: 4
caggtgcagc tgcagcagtc tggggctgag ctggtgaggc ctgggtcctc agtgaagatt        60
tcctgcaagg cttctggcta tgcattcagt agctactgga tgaactgggt gaagcagagg       120
cctggacagg tcttgagtg gattggacag atttggcctg agatggtga tactaactac         180 aatgaaagt tcaagggtaa agccactctg actgcagacg aatcctccag cacagcctac        240
atgcaactca gcagcctagc atctgaggac tctgcggtct atttctgtgc aagacgggag       300
actacgacgg taggccgtta ttactatgct atggactact ggggccaagg gaccacggtc       360
accgtctcct cc                                                           372

<210> SEQ ID NO 5
<211> LENGTH: 111
<212> TYPE: PRT
<213> ORGANISM: Artificial Sequence
<220> FEATURE:
<223> OTHER INFORMATION: VL anti CD19

<400> SEQUENCE: 5

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 6
<211> LENGTH: 333
<212> TYPE: DNA
<213> ORGANISM: Artificial Sequence
<220> FEATURE:
<223> OTHER INFORMATION: VL anti CD19

<400> SEQUENCE: 6
gatatccagc tgacccagtc tccagcttct ttggctgtgt ctctagggca gagggccacc        60
atctcctgca aggccagcca agtgttgat tatgatggtg atagttattt gaactggtac        120
caacagattc caggacagcc acccaaactc ctcatctatg atgcatccaa tctagtttct       180
gggatcccac ccaggtttag tggcagtggg tctgggacag acttcaccct caacatccat       240
cctgtggaga aggtggatgc tgcaacctat cactgtcagc aaagtactga ggatccgtgg       300
acgttcggtg gagggaccaa gctcgagatc aaa                                    333
```

<210> SEQ ID NO 7
<211> LENGTH: 119
<212> TYPE: PRT
<213> ORGANISM: Artificial Sequence
<220> FEATURE:
<223> OTHER INFORMATION: VH anti CD3

<400> SEQUENCE: 7

```
Asp Ile Lys Leu Gln Gln Ser Gly Ala Glu Leu Ala Arg Pro Gly Ala
1               5                   10                  15
Ser Val Lys Met Ser Cys Lys Thr Ser Gly Tyr Thr Phe Thr Arg Tyr
            20                  25                  30
Thr Met His Trp Val Lys Gln Arg Pro Gly Gln Gly Leu Glu Trp Ile
        35                  40                  45
Gly Tyr Ile Asn Pro Ser Arg Gly Tyr Thr Asn Tyr Asn Gln Lys Phe
    50                  55                  60
Lys Asp Lys Ala Thr Leu Thr Thr Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Tyr Tyr Asp Asp His Tyr Cys Leu Asp Tyr Trp Gly Gln Gly
            100                 105                 110
Thr Thr Leu Thr Val Ser Ser
        115
```

<210> SEQ ID NO 8
<211> LENGTH: 357
<212> TYPE: DNA
<213> ORGANISM: Artificial Sequence
<220> FEATURE:
<223> OTHER INFORMATION: VH anti CD3

<400> SEQUENCE: 8

```
gatatcaaac tgcagcagtc aggggctgaa ctggcaagac ctggggcctc agtgaagatg     60
tcctgcaaga cttctggcta cacctttact aggtacacga tgcactgggt aaaacagagg    120
cctggacagg gtctggaatg gattggatac attaatccta gccgtggtta tactaattac    180
aatcagaagt tcaaggacaa ggccacattg actacagaca aatcctccag cacagcctac    240
atgcaactga gcagcctgac atctgaggac tctgcagtct attactgtgc aagatattat    300
gatgatcatt actgccttga ctactggggc caaggcacca ctctcacagt ctcctca      357
```

<210> SEQ ID NO 9
<211> LENGTH: 106
<212> TYPE: PRT
<213> ORGANISM: Artificial Sequence
<220> FEATURE:
<223> OTHER INFORMATION: VL anti CD3

<400> SEQUENCE: 9

```
Asp Ile Gln Leu Thr Gln Ser Pro Ala Ile Met Ser Ala Ser Pro Gly
1               5                   10                  15
Glu Lys Val Thr Met Thr Cys Arg Ala Ser Ser Ser Val Ser Tyr Met
            20                  25                  30
Asn Trp Tyr Gln Gln Lys Ser Gly Thr Ser Pro Lys Arg Trp Ile Tyr
        35                  40                  45
Asp Thr Ser Lys Val Ala Ser Gly Val Pro Tyr Arg Phe Ser Gly Ser
    50                  55                  60
Gly Ser Gly Thr Ser Tyr Ser Leu Thr Ile Ser Ser Met Glu Ala Glu
65                  70                  75                  80
```

Asp Ala Ala Thr Tyr Tyr Cys Gln Gln Trp Ser Ser Asn Pro Leu Thr
            85                  90                  95

Phe Gly Ala Gly Thr Lys Leu Glu Leu Lys
            100                 105

<210> SEQ ID NO 10
<211> LENGTH: 318
<212> TYPE: DNA
<213> ORGANISM: Artificial Sequence
<220> FEATURE:
<223> OTHER INFORMATION: VL anti CD3

<400> SEQUENCE: 10
gacattcagc tgacccagtc tccagcaatc atgtctgcat ctccagggga gaaggtcacc      60
atgacctgca gagccagttc aagtgtaagt tacatgaact ggtaccagca gaagtcaggc     120
acctccccca aaagatggat ttatgacaca tccaaagtgg cttctggagt cccttatcgc     180
ttcagtggca gtgggtctgg gacctcatac tctctcacaa tcagcagcat ggaggctgaa     240
gatgctgcca cttattactg ccaacagtgg agtagtaacc cgctcacgtt cggtgctggg     300
accaagctgg agctgaaa                                                   318

<210> SEQ ID NO 11
<211> LENGTH: 5
<212> TYPE: PRT
<213> ORGANISM: artificial
<220> FEATURE:
<223> OTHER INFORMATION: CD3 CDR-H1

<400> SEQUENCE: 11

Arg Tyr Thr Met His
1               5

<210> SEQ ID NO 12
<211> LENGTH: 17
<212> TYPE: PRT
<213> ORGANISM: artificial
<220> FEATURE:
<223> OTHER INFORMATION: CD3 CDR-H2

<400> SEQUENCE: 12

Tyr Ile Asn Pro Ser Arg Gly Tyr Thr Asn Tyr Asn Gln Lys Phe Lys
1               5                   10                  15

Asp

<210> SEQ ID NO 13
<211> LENGTH: 10
<212> TYPE: PRT
<213> ORGANISM: artificial
<220> FEATURE:
<223> OTHER INFORMATION: CD3 CDR-H3

<400> SEQUENCE: 13

Tyr Tyr Asp Asp His Tyr Cys Leu Asp Tyr
1               5                   10

<210> SEQ ID NO 14
<211> LENGTH: 10
<212> TYPE: PRT
<213> ORGANISM: artificial
<220> FEATURE:
<223> OTHER INFORMATION: CD3 CDR-L1

<400> SEQUENCE: 14

Arg Ala Ser Ser Val Ser Tyr Met Asn
1               5                   10

<210> SEQ ID NO 15
<211> LENGTH: 7
<212> TYPE: PRT
<213> ORGANISM: artificial
<220> FEATURE:
<223> OTHER INFORMATION: CD3 CDR-L2

<400> SEQUENCE: 15

Asp Thr Ser Lys Val Ala Ser
1               5

<210> SEQ ID NO 16
<211> LENGTH: 9
<212> TYPE: PRT
<213> ORGANISM: artificial
<220> FEATURE:
<223> OTHER INFORMATION: CD3 CDR-L3

<400> SEQUENCE: 16

Gln Gln Trp Ser Ser Asn Pro Leu Thr
1               5

<210> SEQ ID NO 17
<211> LENGTH: 5
<212> TYPE: PRT
<213> ORGANISM: artificial
<220> FEATURE:
<223> OTHER INFORMATION: CD19 CDR-H1

<400> SEQUENCE: 17

Ser Tyr Trp Met Asn
1               5

<210> SEQ ID NO 18
<211> LENGTH: 17
<212> TYPE: PRT
<213> ORGANISM: artificial
<220> FEATURE:
<223> OTHER INFORMATION: CD19 CDR-H2

<400> SEQUENCE: 18

Gln Ile Trp Pro Gly Asp Gly Asp Thr Asn Tyr Asn Gly Lys Phe Lys
1               5                   10                  15

Gly

<210> SEQ ID NO 19
<211> LENGTH: 15
<212> TYPE: PRT
<213> ORGANISM: artificial
<220> FEATURE:
<223> OTHER INFORMATION: CD19 CDR-H3

<400> SEQUENCE: 19

Arg Glu Thr Thr Thr Val Gly Arg Tyr Tyr Tyr Ala Met Asp Tyr
1               5                   10                  15

<210> SEQ ID NO 20
<211> LENGTH: 15
<212> TYPE: PRT
<213> ORGANISM: artificial
<220> FEATURE:
<223> OTHER INFORMATION: CD19 CDR-L1

```
<400> SEQUENCE: 20

Lys Ala Ser Gln Ser Val Asp Tyr Asp Gly Asp Ser Tyr Leu Asn
1               5                   10                  15

<210> SEQ ID NO 21
<211> LENGTH: 7
<212> TYPE: PRT
<213> ORGANISM: artificial
<220> FEATURE:
<223> OTHER INFORMATION: CD19 CDR-L2

<400> SEQUENCE: 21

Asp Ala Ser Asn Leu Val Ser
1               5

<210> SEQ ID NO 22
<211> LENGTH: 9
<212> TYPE: PRT
<213> ORGANISM: artificial
<220> FEATURE:
<223> OTHER INFORMATION: CD19 CDR-L3

<400> SEQUENCE: 22

Gln Gln Ser Thr Glu Asp Pro Trp Thr
1               5

<210> SEQ ID NO 23
<211> LENGTH: 5
<212> TYPE: PRT
<213> ORGANISM: Artificial Sequence
<220> FEATURE:
<223> OTHER INFORMATION: Polypeptide spacer

<400> SEQUENCE: 23

Gly Gly Gly Gly Ser
1               5
```

DOSAGE REGIMEN FOR ADMINISTRATING A CD19×CD3 BISPECIFIC ANTIBODY TO PATIENTS AT RISK FOR POTENTIAL ADVERSE EFFECTS

The present invention relates to a method for assessing (analyzing) the risk of potential adverse effects for a human patient mediated by the administration of a CD19×CD3 bispecific antibody to said patient comprising determining the ratio of B cells to T cells or total B cells of said patient, wherein a ratio of about 1:5 or lower and/or a total B cell count of less than about 50 B cells per microliter of peripheral blood is indicative for a risk of potential adverse effects for said patient. Accordingly, the present invention relates to a method (dosage regimen) for administering a CD19×CD3 bispecific antibody to a human patient having a B:T cell ratio of about 1:5 or lower or a total B cell count of less than about 50 B cells per microliter in peripheral blood, comprising (a) administering a first dose of said antibody for a first period of time; and consecutively (b) administering a second dose of said antibody for a second period of time, wherein said second dose exceeds said first dose. In some embodiments, a third dose of said antibody is optionally administered for a third period of time or for the same time period as the first and/or second doses. The third dose of said antibody exceeds said second dose. This dosage regimen can be applied in methods for treating malignant CD19 positive lymphocytes or for ameliorating and/or preventing an adverse effect mediated by the administration of said bispecific antibody. The present invention also relates to the use of a CD19×CD3 bispecific antibody for the preparation of a pharmaceutical composition to be used in a method of the present invention. A pharmaceutical package or kit comprising a first dose and a second dose and optionally a third dose of said antibody as defined in the methods/dosage regimen of the present invention is disclosed as well.

Antibody-based cancer therapies require a target antigen firmly bound to the surface of cancer cells in order to be active. By binding to the surface target, the antibody can directly deliver a deadly signal to the cancer cell or indirectly by, for example, recruiting a cytotoxic T cell, if it is a bispecific antibody. In an ideal treatment scenario, a target antigen is abundantly present and accessible on every cancer cell and is absent, shielded or much less abundant on normal cells. This situation provides the basis for a therapeutic window in which a defined amount of the antibody-based therapeutic effectively hits cancer cells but spares normal cells.

Though antibodies are an effective means in treating many disorders, in particular cancer, their administration is not necessarily devoid of side effects. Adverse effects may cause a reversible or irreversible change in the health status of a patient. As adverse effects could be harmful and undesired, it is highly desirable to avoid them. However, though it is known that a medicament can cause adverse effects, its prescription and administration could not be avoided or is accepted, since the medicament has an outstanding beneficial therapeutic effect or may even be life-saving.

In clinical trials, a general distinction can be made between adverse effects (AEs) and serious adverse effects (SAEs). Specifically, adverse effects can be classified in 5 grades in accordance with the Common Terminology Criteria for Adverse Events (CTCAE). Grade 1 relates to mild AE, Grade 2 to moderate AE, Grade 3 to severe AE, Grade 4 to life-threatening or disabling AE, while Grade 5 means death related to AE.

An adverse effect observed in antibody therapy is the occurrence of infusion-related side effects, such as the cytokine release syndrome ("CRS"). Other adverse side effects described to be associated with CRS are fatigue, vomiting, tachycardia, hypertension, back pain, but also central nervous system reactions (CNS reactions), such as seizures, encephalopathy, cerebral edema, aseptic meningitis, and headache.

Cytokine release and neurological reactions have not only been observed with monoclonal antibodies binding to the T cell receptor but also with a CD19×CD3 bispecific single chain antibody binding to the CD3 part of the T cell receptor (called Blinatumomab (MT103)).

Blinatumomab (MT103) is a lymphoma-directed, recombinant bispecific single-chain CD19×CD3 antibody that binds to CD19 on the surface of almost all B cells and B tumor cells and concomitantly can engage a T cell, thereby triggering the T-cell to kill the target B cell or B tumor cell. Blinatumomab consists of four immunoglobulin variable domains assembled into a single polypeptide chain. Two of the variable domains form the binding site for CD19, a cell surface antigen expressed on most B cells and B tumor cells. The other two variable domains form the binding site for the CD3 complex on T cells. Blinatumomab is designed to direct the body's cytotoxic, or cell-destroying, T cells against tumor cells, and represent a new therapeutic approach to cancer therapy. Blinatumomab is presently in clinical trials.

As described for instance in WO 99/54440, adverse effects have been observed in a previous study performed with Blinatumomab applied in repeated bolus infusions to a patient with B-cell derived chronic lymphatic leukaemia (B-CLL). As shown in FIGS. 19 and 20 of WO 99/54440, release of TNF, IL-6 and IL-8 has been found in response to each of the two administered 20 minute-infusions of 3 microgram and 10 microgram of the mentioned bispecific single chain antibody, respectively, with cytokine release after each administration. Maximal cytokine release was observed after administration of 10 microgram of bispecific single chain antibody. In a following clinical trial study, in which escalating doses of the CD19×CD3 bispecific single chain antibody have been administered to patients with B cell malignancies as bolus infusions, adverse effects have also been observed. According to a retrospective analysis, 7 out of 22 patients showed an early neurological reaction, including, for example, confusion, ataxia, speech disorder, or disorientation.

In order to try to better manage these undesired side effects, the mode of administration of the CD19×CD3 bispecific single chain antibody has been changed in that it has been switched over from bolus infusion to a continuous intravenous administration of said antibody for a longer period of time. As shown in Bargou et al. (Science 321 (2008): 974-7), doses as low as 0.005 milligrams per square meter per day continuously administered to non-Hodgkin's lymphoma patients over four weeks led to an elimination of lymphoma target cells in blood. Partial and complete tumor regressions were first observed at a dose level of 0.015 milligrams/m$^2$/d, and all seven patients treated at a dose level of 0.06 milligrams/m$^2$/d experienced a tumor regression (Bargou et al., cited above). The CD19×CD3 bispecific single chain antibody also led to clearance of tumor cells from bone marrow and liver. However, though this (still ongoing) study established clinical proof of concept for the therapeutic potency of the CD19×CD3 bispecific single chain antibody format in the treatment of blood-cell derived cancer, neurological reactions have been found in the course of the aforementioned clinical trial. Accordingly, since Blinatumomab is a very promising candidate medicament for treating non-Hodgkin's lymphoma (NHL), acute lymphoblastic leukemia (ALL), chronic lymphocytic leukemia (CLL) and/or mantle cell lymphoma, it is highly desirable to reduce or even completely avoid undesired side-effects in the treatment of patients in need thereof with the CD19×CD3 bispecific single chain antibody.

Evidently, it is difficult to design a CD19×CD3 antibody-based therapy, which does not cause CNS (neurological) reactions including neurological reactions, or, to put it differently, it is desired to provide a CD19×CD13 antibody-based medical therapies with increased patient tolerability, i.e., reduced or even no undesired adverse effects such as CNS reactions.

Though pharmaceutical means and methods which allow a more gradual activation of T cell populations (see WO 2007/068354) already helped to avoid significant adverse side effects in patients treated with the CD19×CD3 bispecific single chain antibody, neurological reactions could unfortunately not be prevented by these measures, in particular in cases in which doses of more than 5 to 10 microgram per square meter per day (i.e. 24 h) of the antibody have been administered.

Thus, the technical problem underlying the present invention was to provide methods for assessing the risk of potential adverse effects for a human patient mediated by the administration of a CD19×CD3 bispecific antibody to said patient in order to then devise dosage regimens and methods to overcome the above problem.

The present invention addresses this need and thus provides embodiments concerning methods as well as dosage regimens for administering a CD19×CD3 bispecific antibody to a human patient.

These embodiments are characterized and described herein and reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In view of the adverse events, particularly the CNS events including neurological reactions observed with antibodies, also including the CD19×CD3 bispecific antibody, the finding that the CD19×CD3 bispecific single chain antibody can be administered so that it is tolerated by the patients, if it is administered in accordance with the dosage regimen as provided herein, is definitely remarkable.

Specifically, the present inventors observed that those patients, to whom a CD19×CD3 bispecific antibody was administered, encountered CNS events, if they had a B:T cell ratio of about 1:5 or lower or a total B cell count of less than about 50 B cells per microliter of peripheral blood. Accordingly, the present invention for the first time establishes a low B:T cell ratio or a low total B cell count as a potential high risk factor for the occurrence of adverse effects including neurological reactions in the treatment of malignant CD19 positive lymphocytes occurring in leukemias and lymphomas (see Examples 2, 3 and 4).

Particularly, the inventors of the present application observed that non-Hodgkin lymphoma (NHL) patients and acute lymphoblastic leukemia (ALL) patients with a low B:T cell ratio or a low total B cell count in peripheral blood have an increased risk for the development of an early neurological reaction. This neurological reaction occurs mainly during the first day(s) of treatment with a CD19×CD13 bispecific antibody. In particular, the majority of the neurological reactions occurred after about 12 to 120 hours after start of treatment. These neurological reactions were transient, fully reversible and resolved without sequelae within 3 to 72 hours after stop of the treatment. The inventors made these unexpected observations in various clinical trial studies using the CD19×CD3 bispecific antibody:

Looking at "short-term" (bolus) infusion trials, 7 out of 22 patients had an early neurological reaction. 6 of these 7 patients had a low B:T cell ratio, i.e., a B:T cell ratio of about 1:5 or lower, before treatment. Of the remaining 15 patients without neurological reaction, only 1 patient had a low B:T cell ratio.

In an NHL clinical trial (see Bargou et al., cited above), a total of 39 patients have been treated until August 2008. At this time point, it has been found that all patients with a neurological reaction that led to permanent discontinuation of the CD19×CD3 bispecific antibody treatment had a low B:T cell ratio (i.e., a B:T cell ratio threshold below 1:5). In particular, 5 neurological reactions have been observed in 10 patients with low B:T cell ratio (5/10), while no patient with a high B:T cell ratio (i.e., a B:T cell ratio higher than 1:5) had a neurological reaction that would have led to permanent discontinuation of CD19×CD3 bispecific antibody treatment (0/29).

Thereafter, a specific cohort for patients with low B:T cell ratio and/or a lower total B cell count i.e. an increased risk for early neurological reactions, was established in order to prospectively analyze the outlined theory and to specifically find mitigation steps for the patients at increased risk.

Since establishing these separated cohorts for high risk patients, 8 NHL patients were prospectively treated (data as of July 2009): 6 patients with low B:T cell ratio, 2 patients with high B:T cell ratio. Again no patient with a high B:T cell ratio had a neurological reaction, while 3 out of 6 patients with a low B:T cell ratio had a neurological reaction, leading to discontinuation of the treatment. In sum, 69 NHL patients, including B-cell chronic lymphocytic leukemia (CLL) and mantle cell lymphoma (MCL), have been treated with a CD19×CD3 bispecific antibody, both with bolus infusion and continuous infusion:

Neurological reactions have been observed in 61% of the patients with low B:T cell ratio. In contrast, only 2% of the patients with high B:T cell ratio showed such adverse events (see the following examples).

In another clinical trial phase II study, 15 μg of CD19× CD3 bispecific single chain antibody per square meter patient body surface area per day have been administered to adult ALL patients by continuous infusion for at least four weeks. One out of 11 ALL patients of the high risk group having a B:T cell ratio below 1:5 showed a neurological reaction, leading to discontinuation of the treatment. In contrast, none of the 6 patients of the low risk group having a B:T cell ratio higher than 1:5 showed a neurological reaction.

Moreover, in a retrospective analysis of 39 NHL patients, a baseline B cell to T cell (B:T) ratio in peripheral blood at or below 1:5 to 1:10 was identified as the only predictive factor for the subsequent occurrence of neurological AEs. The predictive value was then prospectively confirmed in 8 additional patients (see Example 1).

These data establish a low B:T cell ratio, i.e., a B:T cell ratio of about 1:5 or lower as a potential high risk factor for the occurrence of adverse effects including neurological reactions in the treatment of malignant CD19 positive lymphocytes occurring in leukemia and lymphoma such as NHL, MCL, CLL and ALL in patients who are treated with a CD19×CD3 bispecific antibody (see Examples 1 and 4).

In addition to utilizing B:T cell ratios as a predictor of CNS events in a patient, it has been determined that initial total B cell counts in the peripheral blood is also a good predictor of CNS events in a patient. In continuing clinical trials, a total of 89 patients undergoing treatment with blinatumomab (70 patients with NHL and 19 patients with ALL) were evaluated. Of these 89 patients, 19 patients had a permanent discontinuation from treatment with blinatumomab due to a CNS event; and low B cell counts of less than about 50 B cells per microliter of peripheral blood in individual patients was useful in identifying these patients susceptible to a CNS event, and correlated with low B:T cell ratios.

More specifically, when all evaluable patients are analyzed by the median of their individual initial B cell count in peripheral blood (median 42.5/microliter), 16 out of 44 patients below this median had a CNS event (36.4%), while 3 out of 44 patients above this median had a CNS event (6.8%); of note: the one patient that represents the median had no CNS event.

Further analyses of this data provide usable cut-offs for separating patients at risk for CNS events leading to permanent discontinuation from blinatumomab treatment based on the initial total B cell count. In view of this data, it has been determined that a total B cell count of less than 35/microliter identifies 16 out of 40 patients with a low B cell count (<35/μL) that showed a CNS event (35.6%) while 3 out of 49 patients with a high B cell count (>35/μl) showed a CNS event (6.1%).

Of note, all 3 patients with the CNS events in the group with high total B cell counts had specifcs that distinguish them from the majority of other patients. For example, 2 patients had received the highest dose of 90 μg/m²/d which was determined as exceeding the MTD as a starting dose and the third patient discontinued treatment only after a break and a re-start of blinatumomab (this was not considered a new treatment cycle and therefore the initial B cell count was used and not the B cell count before the re-start). If the total B cell count before re-start would have been used this patient would also have fallen into the group of patients with a B cell count below 35/μl.

Similarly considering a cut-off to a B cell count of about 50/microliter (50/μl) to assess the risk of adverse effects is almost identical with the median as cut-off; i.e.: 16 out of 45 patients with a low B cell count (<50/μL) showed a CNS event (40.0%) while 3 out of 44 patients with a high B cell count (>50/μl) showed a CNS event (6.7%). See FIG. 1 for a Summary of this information.

Similarly, the median total B cell counts before blinatumomab treatment started were 113.25/μl for all patients without CNS event leading to permanent discontinuation and 1.12/μl for all patients with such a CNS event.

Therefore, a low peripheral B cell count before treatment start is a good predictor for the occurrence of CNS events leading to permanent discontinuation of blinatumomab treatment, and vice versa, a high peripheral total B cell count before treatment started is a good predictor for a reduced occurrence of CNS events leading to permanent discontinuation of blinatumomab treatment (see FIGS. 2A and 2B showing data from two clinical studies applying a CD19× CD3 bispecific antibody). Low total B cell counts of less than 40-50/microliter correlate well with the low B:T cell ratio of less than about 1:8-1:9 and indicates a patient at risk for the occurrence of a CNS event during treatment with blinatumomab.

Thus, it was an aim of the present invention to provide a method that allows identifying patients who may be at a risk of suffering from adverse effects when being treated with a CD19×CD3 bispecific antibody. This method will improve drug compliance, since the identification of patients who are at a risk of suffering from adverse effects allows adjusting the dosage regimen of the CD19×CD3 bispecific antibody. In fact, the present inventors have applied their finding that a B:T cell ratio of about 1:5 or lower and/or a total B cell count of less than about 50 B cells/microliter of peripheral blood could be a potential risk factor for suffering from adverse effects in the treatment with a CD19×CD3 bispecific antibody and have thus developed a dosage regimen which is intended to prevent and/or ameliorate these adverse effects.

Accordingly, in a first aspect the present invention provides a method for assessing (analysing) the risk of potential adverse effects for a human patient mediated by the administration of a CD19×CD3 bispecific antibody to said patient comprising determining in a sample from said patient the ratio of B cells to T cells of said patient, wherein a ratio of about 1:5 or lower and/or a total B cell count of less than about 50 B cells/microliter of peripheral blood is indicative for a risk of potential adverse effects for said patient. On the other hand, a ratio of higher than 1:5 and/or a total B cell count of greater than about 50 B cells/microliter of peripheral blood is indicative for a decreased risk of potential adverse effects for said patients. Thus, the methods of the present invention allow a "grouping" of patients into low and high risk patients. Dependent on the risk group, a patient-tailored treatment regimen should be applied, as described herein.

"Assessing (analysing) the risk" means that the method of the first aspect of the present invention aims at assessing or analysing as to whether or not a patient has a higher or lower likelihood or probability (i.e., an increased or decreased risk, respectively) to encounter adverse effects. Accordingly, as is commonly known, a risk does not necessarily mean that a patient will or will not encounter adverse effects.

In the present invention, when a patient has a B:T cell ratio of about 1:5 or lower and/or a total B cell count of less than about 50 B cells/microliter of peripheral blood, said patient has (is at) an increased risk of potential adverse effects, also including the onset of an adverse effect, while a patient who has a B:T cell ratio higher than 1:5 and/or a total B cell count of greater than about 50 B cells/microliter of peripheral blood does not have (is not at) or at least has (is at) a decreased risk of potential adverse effects, also including the onset of an adverse effect.

Accordingly, a B:T cell ratio of about 1:5 or lower is indicative for a risk of adverse effects, while a B:T cell ratio of higher than 1:5 is not indicative for a risk of adverse effects. Similarly, a total B cell count of less than about 50 B cells/microliter of peripheral blood is indicative for a risk of adverse effects, while a total B cell count of greater than 50 B cells/microliter of peripheral blood is not indicative for a risk of adverse effects.

Thus, the term "indicative for" when used in the context of the method of the first aspect of the present invention means that a patient has an increased risk of potential adverse effects if the B:T cell ratio is about 1:5 or lower and/or if the total B cell count is less than about 50 B cells/microliter of peripheral blood or has a decreased risk of potential adverse effects if the B:T cell ratio is higher than 1:5 and/or a total B cell count of greater than 50 B cells/microliter of peripheral blood.

An "adverse effect" is a harmful and undesired effect resulting from medication in the treatment of a patient with a CD19xCD3 bispecific antibody. An adverse effect may also be termed a "side effect". Some adverse effects only occur only when starting, increasing or discontinuing a treatment. The inventors have observed that the adverse effect seen in the treatment of patients with a CD19xCD3 bispecific antibody occurred after about 12 to 120 hours after the start of the treatment and are reversible.

An adverse effect may cause medical complications. The inventors have observed neurological reactions in patients treated with a CD19xCD3 bispecific antibody. These neurological reaction, unless they can be stopped or avoided, lead to non-compliance with the CD19xCD3 bispecific antibody treatment.

However, as mentioned herein, the inventors found that the B:T cell ratio and/or a total B cell count is an indicator as to whether or not patients are at a risk of potential adverse side effects. Specifically, a B:T cell ratio of about or lower than 1:5 and/or a total B cell count of less than about 50 B cells/microliter of peripheral blood is an indicator that patients are at a risk of potential side effects, while a B:T cell ratio higher than about 1:5 and/or a total B cell count of greater than about 50 B cells/microliter of peripheral blood is an indicator that patients have no or at least have a decreased risk of potential side.

As mentioned before, the method of the first aspect of the present invention is for assessing (analysing) the risk of adverse effects and a risk includes the assessment/analysis of likelihood or a probability. Accordingly, the term "potential" when used in the context of adverse effects means that—though a patient may have a B:T cell ratio of about 1:5 or lower and/or a total B cell count of less than about 50 B cells/microliter of peripheral blood—said patient does not necessarily have to encounter adverse effects.

Likewise, though a patient may have a B:T cell ratio higher than about 1:5 or a total B cell count of greater than about 50 B cells/microliter of peripheral blood—said patient does not necessarily have to not encounter adverse effects. Accordingly, the term "potential" implies that the method of the first aspect of the present invention provides predictions as to whether or not a patient may encounter adverse effects, but—self-explanatory as it is—cannot provide a 100% safe prediction, since, apart from the B:T cell ratio or total B cell count, individual factors such as sex, age, weight, nutritional status, health status, pre-medication etc. may have an influence as to whether or not a patient will encounter adverse effects.

In accordance with the present invention an adverse effect is preferably characterized by a neurological reaction (also sometimes referred to herein as "CNS reaction" or "CNS event", for which reason these terms can be equally used). Said neurological reaction is preferably one or more selected from the group consisting of: confusion, ataxia, disorientation, dysphasia, aphasia, speech impairment, cerebellar symptoms, tremor, apraxia, seizure, grand mal convulsion, palsy, and balance disorder.

The degree of an adverse effect can, for example, be measured in accordance with the NCI Common Terminology Criteria for Adverse Events v3.0 (CTCAE) (Publish Date: Dec. 12, 2003) in grades. A Grade refers to the severity of the adverse effects. The CTCAE v3.0 displays grades 1 through 5 with unique clinical descriptions of severity for each adverse effects:

Grade 1: mild adverse effects
Grade 2: Moderate adverse effects
Grade 3: Severe adverse effects
Grade 4: Life-threatening or disabling adverse effects.
Grade 5: Death of the patient.

A "patient" is a human individual who will be or is treated with a CD19xCD3 bispecific antibody. In accordance with the present invention, the patient is suspected/assumed to comprise or already comprises malignant CD19 positive lymphocytes (in particular B cells). In the latter case, said patient has already been diagnosed to comprise such cells. These malignant CD19 positive lymphocytes (in particular B cells) are present in a patient developing and/or suffering from leukemia and/or lymphoma. In accordance with the present invention a patient is thus in need of a treatment of malignant CD19 positive lymphocytes. Preferably, a patient who will be or is treated with a CD19xCD3 bispecific antibody is (or has been) diagnosed in accordance with the method of the first aspect of the invention as described herein.

A patient may sometimes be called herein a "high risk patient", if his/her total B cell count is less than 50 B cells per microliter of peripheral blood as described herein. Similarly, a patient may sometimes be called herein a "low risk patient", if his/her total B cell count is greater than 50 B cells per microliter of peripheral blood as described herein.

"Mediated by" when used in the context of the method of the first aspect of the present invention means that adverse effects that a patient may or may not encounter are caused by the administration of a CD19xCD3 bispecific antibody. Put it differently, the CD19xCD3 antibody is the causative agent that may cause potential adverse effects in a patient.

The administration may be in the form of a bolus administration or continuous administration, with continuous administration being preferred.

In accordance with the present invention by the term "sample" is intended any biological sample obtained from a human patient containing polynucleotides or polypeptides or portions thereof. Biological samples include body fluids (such as blood, serum, plasma, urine, saliva, synovial fluid and spinal fluid) and tissue sources found to malignant CD19 positive lymphocytes. Methods for obtaining tissue biopsies and body fluids from patients are well known in the art. Generally, a biological sample which includes peripheral blood mononuclear cells (PBMCs), in particular B cells and T cells is preferred as a source.

A sample which includes peripheral blood mononuclear cells (PBMCs), in particular B cells and T cells is preferably taken from peripheral blood of a human patient.

Other preferred samples are whole blood, serum, plasma or synovial fluid, with plasma or serum being most preferred. However, a sample from peripheral blood of a human patient is particularly preferred.

A "B:T cell ratio" as used herein refers to the ratio of the number of B cells and the number of T cells. It is preferably determined in a sample taken from a human patient. Preferably, the sample is taken from the peripheral blood of a human patient. The number of B or T cells, for example, in a peripheral blood sample can be determined by any means usually applied in the art, for example, by FACS analysis.

The B:T cell ratio of the patient population treated according to the present invention is preferably about 1:5 or lower including a B:T cell ratio of about 1:6, 1:7, 1:8, 1:9, 1:10, 1:11, 1:12, 1:13, 1:14, 1:15, 1:20, 1:100, 1:200, 1:400, 1:500, 1:1000, 1:2000, 1:3000, 1:4000, 1:5000 or even lower, with less than about 1:8, 1:9, 1:10, 1:50, 1:100, 1:500, 1:1000 being indicative for a risk of potential adverse effects for said patient.

"Determining the B:T cell ratio" includes
(a) determining the total B cell number in a sample from a patient, preferably in a peripheral blood sample of the patient;
(b) determining the total T cell number in sample from a patient, preferably in a peripheral blood sample of the patient; and
(c) calculating the ratio of the B cell number of step (a) and the T cell number of step (b) in order to obtain a B:T cell ratio.

Of note, a low B:T cell ratio can also be seen as high T:B ratio; and vice versa. Accordingly, the ratios provided herein for a low B:T cell ratio would then have to be reversed.

In contrast, patients showing a B:T cell ratio higher than about 1:5 including a B:T cell ratio of higher than about 1:4, 1:3, 1:2, 1:1, 2:1, 3:1, 4:1, 5:1, 6:1, 7:1, 8:1, 9:1, 10:1 or higher, have a decreased risk of suffering from potential adverse effects upon administration of a CD19×CD3 bispecific antibody. Thus, these patients have higher numbers of B cells as compared to T cells and higher numbers of B cells than compared to the at risk patients for CNS events.

A "total B cell count" as used herein refers to the number of B cells in the patient. It is preferably determined in a sample taken from a human patient. Preferably, the sample is taken from the peripheral blood of a human patient. The number of B cells, for example, in a peripheral blood sample can be determined by any means usually applied in the art, for example, by FACS analysis, and provided by the total number of B cells per microliter of peripheral blood.

The total B cell count in the patient is preferably about 50 B cells/microliter of peripheral blood or greater, including a total B cell count of about 50, 51, 52, 53, 54, 55, 56, 57, 58, 59, 60, 61, 62, 63, 64, 65, 66, 67, 68, 69, 70. 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115 or greater per microliter of peripheral blood being preferred.

Generally, the preferred minimum number of total B cells should preferably be greater than 50 total B cells, more preferably greater than 40, 41, or 42 total B cells or even more preferably greater than 35 total B cells per microliter of peripheral blood as indicative for a lower risk of adverse effects for a patient when treated with a CD19×CD3 bispecific antibody.

Generally, as being indicative for a higher risk of adverse effects for a patient when treated with a CD19×CD3 bispecific antibody, the total B cell count in the patient is preferably less than 50 total B cells per microliter of peripheral blood, more preferably less than 42, 41 or 40 total B cells per microliter of peripheral blood, even more preferably less than 35 total B cells per microliter of peripheral blood.

It is apparent that if the cut-off value for high risk patients would be adjusted from, e.g. less than 50 or 40 B cells per microliter of peripheral blood to less than 35 B cells per microliter of peripheral blood, with less than 35 B cells per microliter of peripheral blood being indicative of a higher risk of adverse effects, then the cut-off value for low risk patients is adjusted accordingly, e.g., from greater than 50 or 40 B cells per microliter of peripheral blood to greater than 35 B cells per microliter of peripheral blood, with greater than 35 B cell per microliter of peripheral blood being indicative of a lower risk of adverse effects.

Accordingly, the present invention also envisages a method for assessing (analysing) the risk of potential adverse effects for a human patient mediated by the administration of a CD19×CD3 bispecific antibody to said patient comprising determining in a sample from said patient the ratio of B cells to T cells of said patient, wherein a ratio of higher than about 1:5 or a total B cell count of greater than about 50 B cells/microliter of peripheral blood is indicative for a decreased risk of potential adverse effects for said patient.

Patients having been assessed to have a decreased risk of potential adverse effects do not necessarily have to be made subject to the two or three stage treatment regimen described herein. Accordingly, these low risk patients can be treated in the normal way, i.e., there is not necessarily a need to start with a low dose and increasing doses over time. These low risk patients can already be treated with a second dose, optionally followed by a third dose as described herein. However, in case these low risk patients when being monitored during therapy may be classified as high risk patients, dependent on the B cell count as described herein and, thus, may have to be subject to the treatment regimen as described herein for high risk patients.

Having observed that patients who have a B:T cell ratio of about 1:5 or lower and/or a total B cell count of lower than about 50 B cells/microliter of peripheral blood are at an increased risk of potential adverse effects, the inventors developed a concept that allows the treatment of these patients with a CD19×CD3 bispecific antibody. Bearing this in mind, it has been elucidated that the T cells of such high risk patients have to be pre-adapted or partially activated by the administration of a low dose of antibody for several days before the dose can then be escalated. So it has been found that a significant decrease in dose given per time unit potentially increases tolerability to said antibody in the high risk patients. In essence, the inventors found that "adapting" a patient to a CD19×CD3 bispecific antibody prior to the therapy with a CD19×CD3 bispecific antibody is beneficial for avoiding undesired adverse effect (particularly the unwanted neurological reactions) (see Examples 6 and 7).

Accordingly, the present invention relates in a second aspect to a method (dosage regimen) for administering a CD19×CD3 bispecific antibody to a human patient having a B:T cell ratio of about 1:5 or lower and/or less than a total B cell count of 50 B cells/microliter of peripheral blood, comprising:
(a) administering a first dose of said antibody for a first period of time; and consecutively
(b) administering a second dose of said antibody for a second period of time;
wherein said second dose exceeds said first dose.

In a further embodiment, the present invention relates to a method (dosage regimen or dosage schedule) for treating identified human patients at risk for potential adverse effects as a result of treatment by the administration of a CD19×CD3 bispecific antibody by ameliorating and/or preventing potential adverse effects comprising:
(a) determining the ratio of B cells to T cells and/or total B cells in a sample from said patient;
(b) identifying human patients at risk for potential adverse effects based on the results of the determining step; and
(c) administering the CD19×CD3 bispecific antibody to the identified human patients at risk for potential adverse effects according to a specific dosage schedule to reduce the possibility of potential adverse effects in said human patients.

The method identifies patients with a total B cell count of less than about 50 B cells per microliter of peripheral blood of said patient as indicative for a risk of potential adverse effects for said patient. Or alternatively, the method identifies patients with a ratio of B cells to T cells of about 1:5 or lower in a sample of peripheral blood of said patient as indicative for a risk of potential adverse effects for said patient.

The method of the present invention provides for the specific dosage schedule for said patient comprises:
(c1) administering a first dose of a CD19×CD3 bispecific antibody for a first period of time; and consecutively
(c2) administering a second dose of said antibody for the first period of time or for a second period of time; and optionally consecutively, and
(c3) administering a third dose of said antibody for the first or second period of time or for a third period of time, wherein said second dose exceeds said first dose and said third dose exceeds said second dose.

The method of the present invention further comprising periodically determining the ratio of B cells to T cells and/or total B cell counts during administration of said antibody.

Additionally, the method also provides that the specific dosage schedule may be adjusted based upon the results of periodically determining the ratio of B cells to T cells and/or total B cell count to reduce the risk for potential adverse effects during the treatment.

It will be understood that in the context of the present invention, the term "method" includes a "dosage regimen" to be used in a method of the present invention.

In the context of the present invention "administration of a CD19×CD3 bispecific antibody" or "administering a CD19×CD3 bispecific antibody" or any other grammatical form thereof means that the CD19×CD3 antibody is in the form of a pharmaceutical composition, optionally comprising a pharmaceutically acceptable carrier. Accordingly, it is to be understood that a pharmaceutical composition comprising a CD19×CD3 bispecific antibody is administered to a human patient.

The term "administering" in all of its grammatical forms means administration of a CD19×CD3 bispecific antibody (in the form of a pharmaceutical composition) either as the sole therapeutic agent or in combination with another therapeutic agent. It is thus envisaged that the pharmaceutical composition of the present invention are employed in co-therapy approaches, i.e. in co-administration with other medicaments or drugs, for example, other medicaments for treating malignant CD19 positive lymphocytes in a patient and/or any other therapeutic agent which might be beneficial in the context of the methods of the present invention.

For example, if the methods of the invention are carried out for the treatment of B-lineage acute lymphoblastic leukemia or aggressive NHL, it can advantageously be combined with intrathecal chemotherapy in order to eliminate target B cells from the CNS. For example, the intrathecal chemotherapy could be performed prior to the administration of the CD19×CD3 bispecific single chain antibody according to the methods described herein.

The administration of a pharmaceutical composition referred to herein is preferably an intravenous administration. It follows that in the methods of the present invention the route of administration in step (a) and/or the route of administration in step (b) is intravenous. It may be administered as a bolus injection or continually (continuously), with continually being preferred.

The administration of a CD19×CD3 bispecific antibody (for example in the form of a pharmaceutical composition) can be a bolus injection or continually or as also sometimes used herein continuously, with continually or continuously being preferred. A continual administration refers to an administration which is essentially without interruption. "Essentially without interruption" includes a continual administration usually without an uninterrupted flow or spatial extension.

In some embodiments, said first dose is not therapeutically active, i.e. it is a subtherapeutic dose. Without being strictly bound, for the purpose of the present invention a dose of 5 µg/m²/d or lower is held to be subtherapeutic.

In a preferred embodiment of the present invention the second dose is therapeutically active. By "therapeutically effective amount" or "therapeutically active" is meant a dose of a CD19×CD3 bispecific antibody that produces the therapeutic effects for which it is administered.

The exact dose will depend on the purpose of the treatment, and will be ascertainable by one skilled in the art using known techniques. As is known in the art and described above, adjustments for age, body weight, general health, sex, diet, drug interaction and the severity of the condition may be necessary, and will be ascertainable with routine experimentation by those skilled in the art. The therapeutic effect of the respective methods or method steps of the present invention is additionally detectable by all established methods and approaches which will indicate a therapeutic effect. It is, for example, envisaged that the therapeutic effect is detected by way of surgical resection or biopsy of an affected tissue/organ which is subsequently analyzed by way of immunohistochemical (IHC) or comparable immunological techniques. Alternatively it is also envisaged that the tumor markers in the serum of the patient (if present) are detected in order to diagnose whether the therapeutic approach is already effective or not. Additionally or alternatively it is also possible to evaluate the general appearance of the respective patient (fitness, well-being, decrease of tumor-mediated ailment etc.) which will also aid the skilled practitioner to evaluate whether a therapeutic effect is already there. The skilled person is aware of numerous other ways which will enable him or her to observe a therapeutic effect of the compounds of the present invention.

In a third aspect, the present invention relates to a method for treating malignant CD19 positive lymphocytes in a human patient having a B:T cell ratio of about 1:5 or lower and/or less than a total B cell count of 50 B cells/microliter of peripheral blood, said method comprising:
(a) administering a first dose of a CD19×CD3 bispecific antibody for a first period of time; and consecutively
(b) administering a second dose of said antibody for a second period of time;
wherein said second dose exceeds said first dose.

Malignant CD19 positive lymphocytes (in particular B cells) are found in leukemia and/or lymphoma. Accordingly, the CD19 positive lymphocytes are in a preferred embodiment lymphoma or leukemia cells.

"Malignant" describes lymphocytes (in particular B cells) that contribute to a progressively worsening disease, in particular lymphoma or leukemia and the diseases described herein. The term is most familiar as a description of cancer, here lymphoma and leukemia and the diseases described herein. Malignant CD19 positive lymphocytes (in particular B cells) are not self-limited in their growth, are capable of invading into adjacent tissues, and may be capable of spreading to distant tissues (metastasizing). Malignant when used herein is synonymous with cancerous.

However, as "normal" (non-malignant) lymphocytes (in particular B cells) also express CD19, it is to be expected that the CD19×CD3 bispecific antibody also binds these normal lymphocytes (in particular B cells) and upon recruiting cytotoxic T cells (because of the second specificity of the bispecific CD19xCD13 antibody) depletes these normal B cells. Yet, it is expected that the population of these normal B cells is reconstituted in the absence of the CD19×CD3 bispecific antibody. It was observed by Leandro and co-workers that after their depletion by an anti-CD20 antibody, B cells were reconstituted in rheumatoid arthritis patients (Arthritis Rheum. 2006 February: 54(2):613-20). As CD20, likewise CD19 is expressed on almost all B cells, it can be expected that B cells upon depletion by the bispecific CD19×CD3 antibody are reconstituted, too.

The lymphoma is preferably indolent or aggressive B cell non-Hodgkin lymphoma (B NHL), mantle cell lymphoma (MCL) or chronic lymphatic leukemia (CLL). Within the meaning of the invention, the term "B cell non-Hodgkin lymphoma" or "B cell derived non-Hodgkin lymphoma" comprises both indolent and aggressive B cell non-Hodgkin lymphoma (B NHL). The term "indolent or aggressive B cell non-Hodgkin lymphoma (B NHL)" as used herein represents malignant B cell-derived tumorous diseases. Indolent B NHL are low malignant lymphomas. Aggressive B-NHL are high malignant lymphomas. The B cell non-Hodgkin lymphoma (B NHL) may advantageously be a follicular lymphoma, lymphoplasmacytic lymphoma, marginal zone cell lymphoma, mantle cell lymphoma (MCL), diffuse large B cell lymphoma (DLBCL), Burkitt's lymphoma, small lymphocytic lymphoma (SLL/CLL) and any other B cell derived subtype. The term "B cell leukemia" as used herein may advantageously be any B cell leukaemia (e.g. chronic lymphocytic leukaemia or acute lymphocytic leukaemia). For further reference see e.g. http://www.cancer.org. Preferably, indolent non-Hodgkin B cell lymphoma may be treated with a bispecific single chain antibody directed against both human CD3 and human CD19 as demonstrated in the following examples.

The leukemia is preferably B-lineage acute lymphoblastic leukemia (ALL).

In a fourth aspect, the present invention relates to a method for ameliorating and/or preventing an adverse effect mediated by the administration of a CD19×CD3 bispecific antibody to a human patient having a B:T cell ratio of about 1:5 or lower and/or less than a total B cell count of 50 B cells/microliter of peripheral blood, said method comprising:
(a) administering a first dose of said antibody for a first period of time, and consecutively
(b) administering a second dose of said antibody for a second period of time;
wherein said second dose exceeds said first dose.

The adverse effect is preferably a neurological reaction, preferably one or more selected from the group consisting of: confusion, ataxia, disorientation, dysphasia, aphasia, speech impairment, cerebellar symptoms, tremor, apraxia, seizure, grand mal convulsion, palsy, and balance disorder (see also Examples 2 and 3).

Specifically, neurological reactions observed during the starting phase of treatment with the CD19×CD3 bispecific antibody include for example confusion and disorientation. "Confusion" as used herein refers to loss of orientation which is the ability to place oneself correctly in the world by time, location, and personal identity, and often memory which is the ability to correctly recall previous events or learn new material. The patients usually have difficulties to concentrate and thinking is not only blurred and unclear but often significantly slowed down. Patients with neurological reactions also suffer from loss of memory. Frequently, the confusion leads to the loss of ability to recognize people and/or places, or to tell time and the date. Feelings of disorientation are common in confusion, and the decision-making ability is impaired. Neurological reactions further comprise blurred speech and/or word finding difficulties. This disorder may impair both, the expression and understanding of language as well as reading and writing. Besides urinary incontinence, also vertigo and dizziness may accompany neurological reactions in some patients.

The occurrence of neurological reactions in the treatment of B cell dependent lymphatic or leukemic malignancies with the CD19×CD3 bispecific antibody may be further influenced by the following factors:

1. Presence of Drug

The CD19×CD3 bispecific antibody retargets T cell cytotoxicity to malignant CD19 positive lymphocytes present, for example, in B cell lymphoma or leukemia cells. In light of this, it can be reasonably assumed that it is the presence of CD19×CD3 bispecific antibody in the body of a patient which is responsible for the adverse effects. Furthermore, side effects are observed only in parts of the body where the CD19×CD3 bispecific antibody is biologically active. Accordingly, neurological reactions upon treatment with the CD19×CD3 bispecific antibody are assumed to be dependent on the presence of said antibody in the cerebrospinal fluid (CSF; liquor) of the patient. This may be supported by the fact that the CD19×CD3 bispecific antibody as well as T cells have only been found in the CSF of NHL patients with a low B:T cell ratio. As explained herein, this patient population has an increased risk for the development of neurological reactions upon antibody treatment. This finding may suggest that the CD19×CD3 bispecific antibody is able to enter the perivascular space dividing the blood vessels and the CNS (including the brain), in high risk NHL and ALL patients. There, the CD19×CD3 bispecific antibody may then engage T cells to target local B cells (either benign or malign) which possibly leads to local cytokine release which in turn could cause neurological reactions.

2. Drug Dose

Further, the neurological reactions seem to be dependent on the dose of the CD19×CD3 bispecific antibody. For example, neurological reactions have not been observed upon continuous administration of 5 µg/m² body surface area of CD19×CD3 bispecific antibody, but with 15 µg/m² body surface area or more CD19×CD3 bispecific antibody in the high risk group of patients. For this reason, as mentioned herein, a dose of less than 5 µg/d/m² is deemed to be subtherapeutic. The effect of the drug dose is evident from the data shown in the appended examples. This observation may imply a dose dependency of neurological reactions in high risk patients with low B:T cell ratio and/or low total B cell counts.

3. Presence of Target Cells and Effector Cells

As set forth above, the neurological reactions upon CD19×CD3 bispecific antibody-treatment are assumed to depend on the presence of i) target cells, i.e. CD19-antigen carrying B cells and ii) effector cells, i.e. cytotoxically active T cells carrying the CD3 antigen, in the PVS/CNS.

In view of this, it is intriguing to hypothesize that the depletion of e.g. the target B cell from the PVS/CNS should result in the avoidance of neurological reactions. In fact, this is exactly what has been observed in the mentioned phase II study in which B lineage acute lymphoblastic leukemia (ALL) patients are being currently treated with the CD19×CD3 bispecific antibody:

In ALL, there is generally a high incidence of leukemic lesions in the CNS. Therefore, each of the ALL patients enrolled in the clinical phase II study referred to herein had received standard ALL therapies in the past, including methotrexate i.v. and/or intrathecal chemotherapy, in order to prevent central nervous system relapses. Some of them received in addition irradiation of the neuroaxis. The ALL patients thereafter received a consolidation therapy, i.e. they obtained several four week-treatment cycles of continuous administration of 15 µg/d/m² of CD19×CD3 bispecific antibody. Only one of the thus far enrolled 17 ALL patients who have been treated with the CD19×CD3 bispecific antibody has developed neurological reactions. This patient was one out of 11 patients belonging to the high risk group having a B:T cell ratio lower than 1:5. None of the six patients of the low risk group with a B:T cell ratio higher than 1:5 showed neurological reactions. It is therefore hypothesized that the mentioned (pre-symptomatic) central nervous system (CNS) treatment reduced the risk of a neurological reaction in the ALL patient in that the B lymphocytic target cells have been removed from the PVS and CNS, including the brain. However, in the absence of B target cells in these tissues, there is no full activation of the cytotoxic T cells. Therefore, less frequent neurological reactions could be observed in said patient populations (see also FIGS. 2A and 2B)

Accordingly, the absence of one of the above factors, in the mentioned case the presence of target B cells in the PVS/CNS, could possibly help to prevent neurological reactions. However, for example, intrathecal chemotherapy is not the therapy of choice in NHL treatment. For instance, it is not effective in indolent NHL therapy, and it is not yet known whether it could be a treatment option for aggressive NHL. In addition, intrathecal chemotherapy is highly toxic for ALL patients and therefore associated with considerable health risks.

In light of the above, the depletion of any one of the above indicated factors without losing therapeutic efficacy is no trivial task since it is for example not easily possible to avoid the presence of B cells in the PVS/CNS of NHL. Furthermore, it has also been found that other measures, including the pre- or co-administration of high doses of steroids could not prevent neurological reactions in the high risk patients.

However, by way of applying the methods/dosage regimens of the present invention, it is possible to ameliorate and/or prevent adverse effects for patients who are at an increased risk of such adverse effects if they have a B:T cell ratio of about 1:5 or lower and/or a total B cell count of less than 50 B cells/microliter of peripheral blood. The present invention envisages providing dosage regimens (methods) which are even independent of the above mentioned factors that could influence a treatment with a CD19×CD3 bispecific antibody.

Thus, the present invention in a preferred aspect relates to a method for assessing (analysing) the risk of potential adverse effects for a human patient mediated by the administration of a CD19×CD3 bispecific antibody to said patient comprising determining the ratio of B cells to T cells in a sample from said patient, wherein a ratio of about 1:5 or lower or determining a total B cell count in a sample from a patient, wherein a total B cell count of less than 50 B cells/microliter of peripheral blood, is indicative for a risk of potential adverse effects for said patient, wherein said patient is (a) administered a first dose of said antibody for a first period of time; and is consecutively (b) administered a second dose of said antibody for a second period of time;

wherein said second dose exceeds said first dose; for (i) treating malignant CD19 positive lymphocytes; and/or (ii) for ameliorating and/or preventing an adverse effect mediated by the administration of a CD19×CD3 bispecific antibody.

Preferably, in this preferred aspect, the patient is administered a third dose of said antibody for a third period of time as described in herein below. Accordingly, the embodiments and aspects described herein in the context of the three-stage method (dose regimen) are applicable to this preferred aspect.

In one aspect of the methods of the present invention said second period of time exceeds said first period of time. The term "exceeds" means that the second period of time is at least one day longer than the first period of time.

Each of the methods (dosage regimens) of the present invention can be repeated, for example, for one, two, three, four, five, six, or more times and in any event as often as there is a beneficial effect for a patient in ameliorating and/or treating malignant CD19 positive lymphocytes, thereby treating lymphoma or leukemia. Dependent on the ratio of the B:T cell ratio and/or total B cell count of a patient, in accordance with the teaching of the present invention, the practitioner can decide as to whether the patient has to be "adapted" to a further treatment with a CD19×CD3 bispecific antibody prior by applying the dosage regimens of the present invention (i.e., administering a low dose of a CD19×CD3 bispecific antibody prior to administering a higher dose in order to "adapt" the patient).

In one embodiment, the dosage of the bispecific antibody can be calculated. For example based upon the data showing the importance of the B:T cell ratio and/or total B cell count in determining the appropriate dose of the CD19×CD3 bispecific antibody in the population of patients at risk for CNS events, a calculation or formula may be used to assist the practitioner in determining appropriate dosages for this patient population. This formula is based on the relationship of the CD19×CD3 bispecific antibody (blinatumomab) dose and the B and T cell counts. For example, $$c \text{ (contant factor)} = \frac{CD19 \times CD3 \text{ bispecific antibody dose} \times T \text{ cell count}}{B \text{ cell count}};$$

meaning that $$CD19 \times CD3 \text{ bispecific antibody\_dose} = \frac{c \times B \text{ cell count}}{T \text{ cell count}}$$

or alternatively,
individualized doses based upon individual patient's B:T cell ratio or total B cell counts can be utilized, where the bispecific antibody dose is calculated by multiplying either the B:T cell ratio or total B cell count by the Constant factor.

It must be understood that the dose or day ranges given herein are illustrated by increments of one, two, three, four or five. These ranges, however, in case of increments higher than one also encompass smaller increments, for example those exemplified by increments of one (10 to 30 includes for example 10, 11, 12, 13, 13 etc. up to 30), or still smaller increments, for example values after the decimal point.

In another aspect of the present invention, it is envisaged that said first period of time is at least 3 days long, whereby even longer periods of time of for example 8, 9, 10, 11, 12, 13 or 14 days are not excluded. "Longer" is thereby not limited to a (one) complete day as the lowest time unit, i.e. ½ days, or fully hours are also conceivable. It is however preferred that the smallest time unit is one full day. Accordingly, said first period of time exceeds 3 days. More preferably, it is envisaged that said first period of time is between 3 days and 10 days, with 7 days being particularly preferred.

As used herein, a time interval which is defined as "X to Y" equates with a time interval which is defined as "between X and Y". Both time intervals specifically include the upper limit and also the lower limit. This means that for example a time interval "3 to 10 days" or between "3 to 10 days" includes a period of time of one, two, three, four, five, six, seven and/or eight days.

As mentioned herein, the inventors observed that "adapting" a human patient having a B:T cell ratio of about 1:5 or lower to the treatment with a CD19×CD3 bispecific antibody during a first period of time allows the treatment of the human patient with an increased second dose of the antibody for a second period of time, whereby adverse effects (in particular neurological reactions) can be better controlled, i.e., could be avoided or at least kept within an acceptable grade in accordance with the CTCAE.

However, for achieving this improvement it is required to "adapt" the human patient having a B:T cell ratio of about 1:5 or lower and/or a total B cell count of less than 50 B cells/microliter of peripheral blood to the CD19×CD3 bispecific antibody by administering a first dose of the antibody for a first period of time (wherein said first dose is lower than the consecutive (second) dose). The administration can be a bolus injection or a continuous administration, whereby a continuous administration is preferred.

Likewise the duration of the first period of time, the duration of the second period of time may be variable in view of, for example, the age, sex, body weight, etc. of the human patient.

Accordingly, in another aspect of the present invention, it is envisaged that said second period of time is at least 18 days long, whereby even longer periods of time of for example 19, 20, 25, 30, 35, 40, 45, 49, 50, 55, 60, 65, 60, 65, 70, 75, 80, 81, 82, 83, 84, 85, 86, 87, 88 or 90 days are not excluded. "Longer" is thereby not limited to a (one) complete day as the lowest time unit, i.e. ½ days, or fully hours are also conceivable. It is however preferred that the smallest time unit is one full day.

Accordingly, said second period of time exceeds 18 days. More preferably, it is envisaged that said second period of time is between 18 days and 81 days, with 21 or 49 days being particularly preferred.

As used herein, a time interval which is defined as "X to Y" equates with a time interval which is defined as "between X and Y". Both time intervals specifically include the upper limit and also the lower limit. This means that for example a time interval "18 to 81 days" or between "18 to 81 days" includes a period of time of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 61, 62, 63 and/or 64 days.

In a more preferred embodiment of the methods/dosage regimens of the present invention, said first period of time is between 3 days and 10 days, and said second period of time is between 18 and 81 days.

In an even more preferred embodiment, said first period of time is 7 days and said second period of time is 21 or 49 days.

In the clinical trials mentioned herein, it was observed that a dose of 15 μg/m²/d in the treatment of NHL effected tumor shrinkage as could be visualized in computer tomography. It was also observed that a dose of 15 μg/m²/d in the treatment of ALL resulted in minimal residual disease and could even eliminate MRD.

Minimal residual disease (MRD) is the name given, to small numbers of leukemic/lymphoma cells that remain in the patient during treatment or after treatment when the patient is in remission (no symptoms or signs of disease). Up until a decade ago none of the tests used to assess/detect cancer, were sensitive enough to detect MRD. Now, however, very sensitive molecular biology tests are available—based on DNA, RNA or Proteins—and these can measure minute levels of cancer cells in tissue samples, sometimes as low as 1 cancer cell in million normal cells.

In cancer treatment, particularly leukemia, MRD testing has several important roles: determining whether treatment has eradicated the cancer or whether traces remain, comparing the efficacy of different treatments, monitoring patient remission status and recurrence of the leukemia or cancer and choosing the treatment that will best meet those needs (personalization of treatment)

Accordingly, in a further aspect of the methods/dosage regimens of the present invention, said first dose is between 1 and 15 μg/m²/d, i.e. 1, 2, 3, 4, 5, 6, 7, 8, 9, 10, 11, 12, 13, 14, 15 μg/m²/d. Particularly preferred is a dose of 5 or 15 μg/m²/d.

As used herein, a dose interval which is defined as "between X and Y" equates with a dose interval which is defined as "X to Y". Both dose intervals specifically include the upper limit and also the lower limit. This means that for example a dose interval "between 1 and 15" or "1 to 15" includes a dose of 1, 2, 3, 4, 5, 6, 7, 8, 9, 10, 11, 12, 13, 14, 15 μg/m²/d. "d" denotes one day.

"m²" denotes a square meter of a patient's body surface (BSA). The "normal" average BSA is generally taken to be about 1.73 m² for an adult, for a neonate it is about 0.25 m², for a 2 year old child it is about 0.5 m², for a 9 year old child it is about 1.07 m², for a 10 year old child it is about 1.14 m², for a 12-13 year old child it is about 1.33 m², for men it is about 1.9 m² and for women it is about 1.6 m².

However, the BSA can also be calculated more precisely by one of the following formulas (each of these formulas can be applied when calculating the BSA):

The Mosteller formula (Mosteller, N Engl J Med 1987 Oct. 22; 317(17): 1098):

BSA (m$^2$)=([Height (cm)×Weight (kg)]/3600)$^{1/2}$ or in inches and pounds:

BSA (m$^2$)=([Height (in)×Weight (lbs)]/3131)$^{1/2}$

The DuBois formula (DuBois, Arch Int Med 1916 17:863-871):

BSA (m$^2$)=0.007184×Height (cm)$^{0.725}$×Weight (kg)$^{0.425}$

The Haycock formula (Haycock, The Journal of Pediatrics 1978 93:1: 62-66):

BSA (m$^2$)=0.024265×Height (cm)$^{0.3964}$×Weight (kg)$^{0.5378}$

The Gehan formula (Gehan, Cancer Chemother Rep 1970 54:225-35):

BSA (m$^2$)=0.0235×Height (cm)$^{0.42246}$×Weight (kg)$^{0.51456}$

The Boyd formula (Boyd, University of Minnesota Press, 1935)

BSA (m$^2$)=0.0003207×Height (cm)$^{0.3}$×Weight (grams)$^{(0.7285-(0.0188 \times log\ 10(grams)}$ It is generally preferred that each of the doses disclosed herein can be converted from amount in μg/m$^2$/d into μg/d by multiplying the respective dose with the factor 1.9. Accordingly, each of the doses disclosed herein can be applied in the methods and uses by multiplying it with the factor 1.9. For example, a dose of 5 μg/m$^2$/d is converted into 9.5 μg/d, a dose of 15 μg/m$^2$/d is converted into 28.5 μg/d and a dose of 60 μg/m$^2$/d is converted into 114 μg/d. It is preferred that a decimal digit that results from the multiplication is either rounded up or rounded down, respectively, to a whole number. For example, a dose of 9.5 μg/d can be rounded down to 9 μg/d and a dose of 28.5 μg/d can be rounded down to 28 μg/d, and after rounding the 60 μg/m$^2$/d dose, it can also be converted to e.g. 112 μg/d (4×28 μg/d). Likewise, a dose of 9.5 μg/d can be rounded up to 10 μg/d and a dose of 28.5 μg/d can be rounded up to 29 μg/d. One skilled in the art can convert the dosing from amount μg/m$^2$/d into μg/d and rounding up or down to obtain an equivalent dose using the factor of 1.9.

The term "μg" [microgram] includes "μg of the CD19× CD3 bispecific antibody preparation". It is preferred that not more than 10% of said CD19×CD3 bispecific antibody preparation is incorrectly folded. It follows that in a preferred embodiment, 90%, 91%, 92%, 93%, 94%, 95%, 96%, 97%, 98%, 99% or even 100% of the CD19×CD3 bispecific antibody is correctly folded. It is also conceivable that the antibody preparation may optionally comprise further ingredients, for example a lyoprotectant, a surfactant, a filler, a binder, and/or bulking agent etc. The amount of such further ingredients is, preferably, not included in the term "μg" as used in the context of the "dose" and/or methods (dosage regimens) of the present invention.

A dose of, for example, 1 μg/m$^2$/d means that 1 μg of the CD19×CD3 bispecific antibody is administered evenly or continuously across one day per square meter body surface. "Continuously across one day" refers to an infusion which is allowed to proceed permanently without interruption.

In a further aspect of the methods/dosage regimen of the present invention, said second dose is between 15 and 60 or 15 and 90 μg/m$^2$/d, i.e. 15, 20, 25, 30, 35, 40, 45, 50, 55 and 60 μg/m$^2$/d or 15, 20, 25, 30, 35, 40, 45, 50, 55, 60, 70, 80 and 90 μg/m$^2$/d. Particularly preferred is a dose of 60 or 90 μg/m$^2$/d. Said second dose is thus therapeutically active. In a preferred embodiment, said first dose is between 5 and 15 μg/m$^2$/d and said second dose is between 15 and 60 or 15 and 90 μg/m$^2$/d.

As used herein, a dose interval which is defined as "between X and Y" equates with a dose interval which is defined as "X to Y". Both dose intervals specifically include the upper limit and also the lower limit. This means that for example a dose interval "between 15 and 60" or "15 to 60" includes a dose of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 and/or 60 μg/m$^2$/d.

It must be understood that the ranges given herein are illustrated by increments of five. These ranges, however, also encompass smaller increments, for example those exemplified by increments of one (10 to 30 includes for example 10, 11, 12, 13, 13 etc. up to 30), or still smaller increments, for example values after the decimal point.

In a further aspect to reduce the risk of the possibility of adverse effects, particularly CNS adverse effects, the methods/dosage regimen or schedule should be administered with the intent to reduce the initial treatment intensity of the CD19×CD3 bispecific antibody to the patient. For example, an approach to reducing the initial treatment would include a step up dosage regimen or schedule to "adapt" the patient, beginning with an initial dosage of the CD19×CD3 bispecific antibody of between 5 and 15 μg/m$^2$/d [or between 9-10 μg/d and 28-29 μg/d] with a further step up in a second dose of 30, 45 or 60 μg/m$^2$/d [57 μg/d, 85-86 μg/d or 112-116 μg/d, respectively] in gradual steps. Flating dosing can be utilized for each of these dosages using the conversion factor of 1.9 and rounding up or down. Also dosage regimens of 5 μg/m$^2$/d to 15 μg/m$^2$/d initially to 45 μg/m$^2$/d then to 60 μg/m$^2$/d either gradually, or in step that could jump some of the intermediate dosage levels if no adverse side effects were observed. Further, dosage regimens or schedules could include administration of 5 μg/m$^2$/d that is increased to 15 μg/m$^2$/d and then to 60 μg/m$^2$/d or as 5 μg/m$^2$/d or 15 μg/m$^2$/d dosage regimens or schedules that are increased to 60 μg/m$^2$/d over time. The practitioner can increase the dosage of the bispecific antibody if the B:T cell ratios and/or total B cell counts continue to remain in the low risk category for adverse effects (a B:T cell ration of 1:5 or lower and/or a total B cell count of less than 50 B cells per microliter of peripheral blood), and particularly CNS adverse effects. But the practitioner should also consider the proper dosage regiment to obtain efficacious results for the disease being treated by the CD19×CD3 bispecific antibody, and balance the efficacy of the antibody with the reduction in risk of adverse effects.

Preferably, not included in the methods for administering a CD19×CD3 bispecific antibody, for treating malignant CD19 positive lymphocytes, or for ameliorating and/or preventing an adverse effect mediated by the administration of a CD19×CD3 bispecific antibody are the following administration schemes:

(i) 5 μg/m$^2$ of the bispecific antibody for one day followed by administration of 15 μg/m$^2$ as daily dose for the remaining period (second and each further consecutive day); and/or (ii) 15 μg/m$^2$ of the bispecific antibody for one day followed by administration of 45 μg/m$^2$ as daily dose for the remaining period (second and each further consecutive day); and/or (iii) 5 μg/m$^2$ of the bispecific antibody for one day followed by administration of 15 μg/m$^2$ for one day, followed by administration of 45 µg/m² as daily dose for the remaining period (third and each further consecutive day); and/or (iv) less than 10-80 µg/m² of the bispecific antibody for one day followed by administration of a dose of 10-80 µg/m² (second and each further consecutive day); and/or (v) less than 10-80 µg/m² of the bispecific antibody for one day followed by administration of a dose of less 10-80 µg/m² for one day, followed by administration of a dose of less 10-80 µg/m² (third and each further consecutive day).

Again flat dosing per day may be used.

As mentioned herein, patients having a B:T cell ratio higher than 1:5 and/or a total B cell count of equal to or greater than 50 B cells/microliter of peripheral blood, do not necessarily have to be adapted to the treatment with a CD19XCD3 bispecific antibody by way of the dosage regimen of the present invention. These patients having a decreased risk of potential adverse effects could be treated by administration of a CD19×CD3 bispecific antibody in a constant dose of 5 µg to 75 µg per square meter body surface area per day for at least four weeks. The administration is preferably a continuous administration.

In another embodiment of the methods (dosage regimen) of the present application, said methods further comprise administering after a first and second dose for a first and second period of time a third dose of said antibody for a third period of time. Accordingly, the present invention provides a three-stage method (dosage regimen).

The administration of said third dose is intravenously. It can be administered in the form of a bolus injection or continuously, with continuously being preferred.

In one aspect of the methods of the present invention said third period of time exceeds said first and second period of time. The term "exceeds" means that the third period of time is at least one day longer than the first and second period of time.

Likewise the duration of the first and second period of time, the duration of the third period of time may be variable in view of, for example, the age, sex, body weight, etc. of the human patient.

In the three-stage dosage regimen aspect of the present invention, it is envisaged that said first period of time is at least 3 days long, whereby even longer periods of time of for example 8, 9, 10, 11, 12, 13 or 14 days are not excluded. "Longer" is thereby not limited to a (one) complete day as the lowest time unit, i.e. IA days, or fully hours are also conceivable. It is however preferred that the smallest time unit is one full day.

Accordingly, said first period of time exceeds 3 days. More preferably, it is envisaged that said first period of time is between 3 days and 10 days, with 7 days being particularly preferred.

As used herein, a time interval which is defined as "X to Y" equates with a time interval which is defined as "between X and Y". Both time intervals specifically include the upper limit and also the lower limit. This means that for example a time interval "3 to 10 days" or between "3 to 10 days" includes a period of time of one, two, three, four, five, six, seven and/or eight days.

In the three-stage dosage regimen aspect of the present invention, it is envisaged that said second period of time is at least 3 days long, whereby even longer periods of time of for example 8, 9, 10, 11, 12, 13 or 14 days are not excluded. "Longer" is thereby not limited to a (one) complete day as the lowest time unit, i.e. ½ days, or fully hours are also conceivable. It is however preferred that the smallest time unit is one full day.

Accordingly, said first period of time exceeds 3 days. More preferably, it is envisaged that said first period of time is between 3 days and 10 days, with 7 days being particularly preferred.

As used herein, a time interval which is defined as "X to Y" equates with a time interval which is defined as "between X and Y". Both time intervals specifically include the upper limit and also the lower limit. This means that for example a time interval "3 to 10 days" or between "3 to 10 days" includes a period of time of one, two, three, four, five, six, seven and/or eight days.

In the three-stage dosage regimen aspect of the present invention, it is envisaged that said third period of time is at least 8 days long, whereby even longer periods of time of for example 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 61, 62, 63, 64, 65, 66, 67, 68, 69, 70 and/or 71 days are not excluded. "Longer" is thereby not limited to a (one) complete day as the lowest time unit, i.e. ½ days, or fully hours are also conceivable. It is however preferred that the smallest time unit is one full day.

Accordingly, said first period of time exceeds 8 days. More preferably, it is envisaged that said first period of time is between 8 days and 78 days, with 14 or 42 days being particularly preferred.

As used herein, a time interval which is defined as "X to Y" equates with a time interval which is defined as "between X and Y". Both time intervals specifically include the upper limit and also the lower limit. This means that for example a time interval "18 to 78 days" or between "18 to 78 days" includes a period of time of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, 50, 52, 54, 56, 58, 60, 61, 62 63, 64, 65, 66, 67, 68, 69, 70 and/or 71 days.

In a more preferred embodiment of the three-stage methods/dosage regimens of the present invention, said first period of time is between 3 days and 10 days, and said second period of time is between 3 days and 10 days, and said third period of time is between 8 days and 78 days.

In an even more preferred embodiment, said first period of time is 7 days, said second period of time is 7 days, and said third period of time is 14 or 42 days.

In an embodiment of the three-stage methods/dosage regimens of the present invention, said third dose exceeds said first and second dose. Said second and third dose are preferably therapeutically active. Of note, said second dose exceeds said first dose.

Accordingly, in a further aspect of the three-stage methods/dosage regimens of the present invention, said first dose is between 1 and 15 µg/m²/d, preferably between 5 and 15 µg/m²/d, i.e. 1, 2, 3, 4, 5, 6, 7, 8, 9, 10, 11, 12, 13, 14, 15 µg/m²/d. Particularly preferred is a dose of 5 or 10 µg/m²/d.

In a further aspect of the three-stage methods/dosage regimens of the present invention, said second dose is between 1 and 15 µg/m²/d, preferably between 5 and 15 µg/m2/d, i.e. 1, 2, 3, 4, 5, 6, 7, 8, 9, 10, 11, 12, 13, 14, 15 µg/m²/d. Particularly preferred is a dose of 15 µg/m²/d.

As used herein, a dose interval which is defined as "between X and Y" equates with a dose interval which is defined as "X to Y". Both dose intervals specifically include the upper limit and also the lower limit. This means that for example a dose interval "between 1 and 15" or "1 to 15" includes a dose of 1, 2, 3, 4, 5, 6, 7, 8, 9, 10, 11, 12, 13, 14, 15 µg/m²/d.

In a further aspect of the three-stage methods/dosage regimen of the present invention, said third dose is between 15 and 60 µg/m²/d, more preferably between 20 and 60

µg/m²/d, i.e. 15, 20, 25, 30, 35, 40, 45, 50, 55 and 60 µg/m²/d. Particularly preferred is a dose of 60 µg/m²/d. Alternatively, said third dose is between 15 and 90 µg/m²/d, more preferably between 60 and 90 µg/m²/d, i.e., 15, 20, 25, 30, 35, 40, 45, 50, 55, 60, 70, 80 and 90 µg/m²/d.

In a preferred embodiment of the three-stage methods/dosage regimen of the present invention, said first dose is between 1 and 15 µg/m²/d, said second dose is between 1 and 15 µg/m²/d, and said third dose is between 15 and 60 or 15 and 90 µg/m²/d.

Particularly preferred, said first dose is 5 µg/m²/d, said second dose is 15 µg/m²/d, and said third dose is 60 µg/m²/d. Alternatively, said third dose may be 90 µg/m²/d.

As used herein, a dose interval which is defined as "between X and Y" equates with a dose interval which is defined as "X to Y". Both dose intervals specifically include the upper limit and also the lower limit. This means that for example a dose interval "between 15 and 60" or "15 to 60" includes a dose of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 and/or 60 µg/m²/d. Similarly, this means that for example a dose interval "between 15 and 90" or "15 to 90" includes a dose of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 86, 87, 88, 89 or 90 µg/m²/d.

In view of the observations made by the present inventors that a three-stage (step) method/dosage regimen aids in avoiding adverse effects as described herein, the present invention relates to a method of treating malignant CD19 positive lymphocytes in a human patient, said method comprising (a) administering a first dose of said antibody for a first period of time; (b) administering a second dose of said antibody for a second period of time; and consecutively (c) administering a third dose of said antibody for a third period of time.

Also, the present invention relates to a method for treating malignant CD19 positive lymphocytes in a human patient, said method comprising (a) administering a first dose of said antibody for a first period of time; (b) administering a second dose of said antibody for a second period of time; and consecutively (c) administering a third dose of said antibody for a third period of time.

Furthermore, the present invention relates to a method for ameliorating and/or preventing an adverse effect mediated by the administration of a CD19×CD3 bispecific antibody to a human patient, said method comprising (a) administering a first dose of said antibody for a first period of time; (b) administering a second dose of said antibody for a second period of time; and consecutively (c) administering a third dose of said antibody for a third period of time.

Preferably, the first, second and third period of time are as described elsewhere herein.

Regarding the doses, it is preferred that the second dose exceeds the first dose and the third dose exceeds the second dose as described elsewhere herein. More preferably, the first dose is 5 µg/m²/d, the second dose is 15 µg/m²/d and the third dose is 60 µg/m²/d. Alternatively, the third dose may also be 90 or 120 µg/m²/d. The equivalent flat doses per day of these doses can be determined by the factor discussed earlier. For example, a dose of 5 µg/m²/d is converted into 9.5 µg/d and rounded to 9 or 10 µg/d, a dose of 15 µg/m² is converted into 28.5 µg/m²/and rounded to 28 or 29 µg/d, and a dose of 60 µg/m²/is converted into 112 µg/m², 114 µg/m² or 116 µg/m² depending upon rounding.

As noted herein above, the present invention relates to methods of treatment/dosage regimen which employ CD19×CD3 bispecific antibodies, comprising a first binding domain capable of binding to an epitope of human CD3 epsilon chain and a second binding domain capable of binding to human CD19. Examples for bispecific molecules according to the methods of the invention are described in great detail in WO 99/54440 and WO 2004/106381 and WO 2008/119565. All the specific CD19×CD3 bispecific antibodies disclosed therein, including their variants, fragments, equivalents etc. are particularly preferred CD19×CD3 bispecific antibodies of the present invention.

As used herein, a "CD19×CD3 bispecific antibody" (including a CD19×CD3 bispecific single chain antibody) denotes a binding entity ("binder") having at least one polypeptide chain comprising two binding domains such as Dual-Affinity Re-Targeting (DART) antibodies, diabodies, domain antibodies (dAbs) or nanobodies. A particularly preferred CD19×CD3 bispecific antibody comprises a single polypeptide chain comprising two binding domains. Such single chain antibodies are preferred in the context of the methods/dosage regimen of the present invention. Each binding domain comprises at least one variable region from an antibody heavy chain ("VH or H region"), wherein the VH region of the first binding domain specifically binds to the CD3 epsilon molecule, and the VH region of the second binding domain specifically binds to CD19. The two binding domains are optionally linked to one another by a short polypeptide spacer. A non-limiting example for a polypeptide spacer is Gly-Gly-Gly-Gly-Ser (G-G-G-G-S) (SEQ ID NO: 23) and repeats thereof. Each binding domain may additionally comprise one variable region from an antibody light chain ("VL or L region"), the VH region and VL region within each of the first and second binding domains being linked to one another via a polypeptide linker, for example of the type disclosed and claimed in EP 623679 B 1, but in any case long enough to allow the VH region and VL region of the first binding domain and the VH region and VL region of the second binding domain to pair with one another such that, together, they are able to specifically bind to the respective first and second binding domains. Such CD19CD3 bispecific single chain antibodies are described in great detail in WO 99/54440 and WO 2004/106381.

The term "binding domain" characterizes in connection with the present invention a domain of a polypeptide which specifically binds to/interacts with a given target structure/antigen/epitope. Thus, the binding domain is an "antigen-interaction-site". The term "antigen-interaction-site" defines, in accordance with the present invention, a motif of a polypeptide, which is able to specifically interact with a specific antigen or a specific group of antigens, e.g. the identical antigen in different species. Said binding/interaction is also understood to define a "specific recognition". The term "specifically recognizing" means in accordance with this invention that the antibody molecule is capable of specifically interacting with and/or binding to at least two, preferably at least three, more preferably at least four amino acids of an antigen, e.g. the human CD3 antigen as defined herein. Such binding may be exemplified by the specificity of a "lock-and-key-principle". Thus, specific motifs in the amino acid sequence of the binding domain and the antigen bind to each other as a result of their primary, secondary or tertiary structure as well as the result of secondary modifications of said structure. The specific interaction of the antigen-interaction-site with its specific antigen may result as well in a simple binding of said site to the antigen. Moreover, the specific interaction of the binding domain/antigen-interaction-site with its specific antigen may alternatively result in the initiation of a signal, e.g. due to the induction of a change of the conformation of the antigen, an oligomerization of the antigen, etc. A preferred example of a binding domain in line with the present invention is an antibody. The binding domain may be a monoclonal or polyclonal antibody or derived from a monoclonal or polyclonal antibody.

The term "antibody" comprises derivatives or functional fragments thereof which still retain the binding specificity. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also comprises immunoglobulins (Ig's) of different classes (i.e. IgA, IgG, IgM, IgD and IgE) and subclasses (such as IgG1, IgG2 etc.).

The definition of the term "antibody" also includes embodiments such as chimeric, single chain and humanized antibodies, as well as antibody fragments, like, inter alia, Fab fragments. Antibody fragments or derivatives further comprise F(ab')2, Fv, scFv fragments or single domain antibodies, single variable domain antibodies or immunoglobulin single variable domain comprising merely one variable domain, which might be VH or VL, that specifically bind to an antigen or epitope independently of other V regions or domains; see, for example, Harlow and Lane (1988) and (1999), cited above. Such immunoglobulin single variable domain encompasses not only an isolated antibody single variable domain polypeptide, but also larger polypeptides that comprise one or more monomers of an antibody single variable domain polypeptide sequence.

As used herein, CD3 epsilon denotes a molecule expressed as part of the T cell receptor and has the meaning as typically ascribed to it in the prior art. In human, it encompasses in individual or independently combined form all known CD3 subunits, for example CD3 epsilon, CD3 delta, CD3 gamma, CD3 zeta, CD3 alpha and CD3 beta. The human CD3 epsilon is indicated in GenBank Accession No. NM_000733. The human CD19 protein is indicated in GenBank Accession No. AAA69966.

Preferably, the bispecific antibody applied in the methods/dosage regimens of the present invention has the domain arrangement VL(CD19)-VH(CD19)-VH(CD3)-VL(CD3). It is, however, also envisaged that the methods of the invention can be carried out with CD19×CD3 bispecific single chain antibodies of other domain arrangements, such as
VH(CD19)-VL(CD19)-VH(CD3)-VL(CD3),
VL(CD19)-VH(CD19)-VL(CD3)-VH(CD3),
VH(CD19)-VL(CD19)-VL(CD3)-VH(CD3),
VL(CD3)-VH(CD3)-VH(CD19)-VL(CD19),
VH(CD3)-VL(CD3)-VH(CD19)-VL(CD19),
VL(CD3)-VH(CD3)-VL(CD19)-VH(CD19), or
VH(CD3)-VL(CD3)-VL(CD19)-VH(CD19).

A preferred CD19×CD3 bispecific antibody applied in the methods of the present invention comprises the
(a) anti-CD3 CDRs of the heavy chain shown as CD3 CDR-H1 in SEQ ID NO: 11 (RYTMH), more preferably residues 26-35 of SEQ ID NO: 7 (GYTFTRYTMH), CD3 CDR-H2 in SEQ ID NO: 12 (YINPSRGYTNYNQKFKD) and CD3 CDR-H3 in SEQ ID NO: 13 (YYDDHYCLDY); and/or (b) anti-CD3 CDRs of the light chain shown as CD3 CDR-L1 in SEQ ID NO: 14 (RASSSVSYMN), CD3 CDR-L2 in SEQ ID NO: 15 (DTSKVAS) and CD3 CDR-L3 in SEQ ID NO: 16 (QQWSSNPLT); and/or
(c) anti-CD19 CDRs of the heavy chain shown as CD19 CDR-H1 in SEQ ID NO: 17 (SYWMN), more preferably residues 26-35 of SEQ ID NO: 3 (GYAFSSYWMN), CD19 CDR-H2 in SEQ ID NO: 18 (QIWPGDGDTNYNGKFKG) and CD19 CDR-H3 in SEQ ID NO: 19 (RETTTVGRYYYAMDY); and/or
(d) anti-CD19 CDRs of the light chain shown as CD19 CDR-L1 in SEQ ID NO: 20 (KASQSVDYDGDSYLN), CD19 CDR-L2 in SEQ ID NO: 21 (DASNLVS) and CD19 CDR-L3 in SEQ ID NO: 22 (QQSTEDPWT).

It is more preferred that the CD19×CD3 bispecific antibody applied in the methods of the present invention comprises the CD3 CDRs of the heavy and light chain. Even more preferably, the CD19×CD3 bispecific antibody applied in the methods of the present invention comprises the CD3 CDRs of the heavy and light chain as well as the CD19 CDRs of the heavy and light chain.

The CDRs referred to herein are in accordance with the Kabat numbering system. The Kabat numbering scheme is a widely adopted standard for numbering the residues in an antibody in a consistent manner (Kabat et al., Sequences of Proteins of Immunological Interest, 1991).

Alternatively, it is preferred that the CD19×CD3 bispecific antibody applied in the methods of the present invention comprises the
(a) CD19 variable heavy chain shown in SEQ ID NO: 3 (nucleotide sequence is shown in SEQ ID NO: 4); and/or
(b) CD19 variable light chain shown in SEQ ID NO: 5 (nucleotide sequence is shown in SEQ ID NO: 6); and/or
(c) CD3 variable heavy chain shown in SEQ ID NO: 7 (nucleotide sequence is shown in SEQ ID NO: 8); and/or
(d) CD3 variable light chain shown in SEQ ID NO: 9 (nucleotide sequence is shown in SEQ ID NO: 10).

More preferably, the CD19×CD3 bispecific antibody applied in the methods of the present invention comprises the CD19 variable heavy and light chain and/or the CD3 variable heavy and light chain. Even more preferably, the CD19×CD3 bispecific antibody applied in the methods of the present invention comprises the CD19 variable heavy and light chain as well as the CD3 variable heavy and light chain.

In another alternative, it is also preferred that said bispecific single chain antibody comprises an amino acid sequence selected from the group consisting of
(a) an amino acid sequence as depicted in SEQ ID NO: 1;
(b) an amino acid sequence encoded by a nucleic acid sequence as shown in SEQ ID NO: 2;
(c) an amino acid sequence encoded by a nucleic acid sequence having at least 70%, 80%, 90%, 95% or 99% identity to a nucleic acid sequence of (b), wherein said amino acid sequence is capable of specifically binding to CD3 and CD19; and
(d) an amino acid sequence encoded by a nucleic acid sequence which is degenerate as a result of the genetic code to a nucleotide sequence of (b), wherein said amino acid sequence is capable of specifically binding to CD3 and CD19.

It is to be understood that the sequence identity is determined over the entire amino acid sequence. For sequence alignments, for example, the programs Gap or BestFit can be used (Needleman and Wunsch J. Mol. Biol. 48 (1970), 443-453; Smith and Waterman, Adv. Appl. Math 2 (1981), 482-489), which is contained in the GCG software package (Genetics Computer Group, 575 Science Drive, Madison, Wis., USA 53711 (1991). It is a routine method for those skilled in the art to determine and identify an amino acid sequence having e.g. 70%, 80%, 90%, 95%, 96%, 97%, 98% or 99% sequence identity to the amino acid sequences of the CD19×CD3 bispecific antibody described herein (preferably MT103). For example, according to Crick's Wobble hypothesis, the 5' base on the anti-codon is not as spatially confined as the other two bases, and could thus have non-standard base pairing. Put in other words: the third position in a codon triplet may vary so that two triplets which differ in this third position may encode the same amino acid residue. Said hypothesis is well known to the person skilled in the art (see e.g., wikipedia.org/wiki/Wobble_Hypothesis; Crick, J Mol Biol 19 (1966): 548-55). It is furthermore a routine procedure for those skilled in the art to determine cytotoxic activity of such an amino acid sequence having e.g. 70%, 80%, 90%, 95%, 96%, 97%, 98% or 99% sequence identity to the nucleotide or amino acid sequences of the CD19×CD3 bispecific single chain antibody described herein. Cytotoxic activity of the CD19×CD3 bispecific single chain antibody or an antibody construct having e.g. 70%, 80%, 90%, 95%, 96%, 97%, 98% or 99% sequence identity to the amino acid sequences of the CD19×CD3 bispecific single chain antibody can be determined by methods as illustrated e.g. in WO 99/54440.

Particularly preferred, said CD19×CD3 bispecific single chain antibody has the amino acid sequence shown in SEQ ID NO: 1.

Also particularly preferred is the CD19×CD3 bispecific antibody MT103 described in WO 99/54440 as well as those CD19×CD3 bispecific antibodies described in WO 2004/106381 and WO 2008/119565.

The present invention furthermore relates to a CD19× CD3 bispecific antibody for:
(i) administering a CD19×CD3 bispecific antibody to a human patient, or
(ii) treating malignant CD19 positive lymphocytes in a human patient; and/or
(iii) ameliorating or preventing an adverse effect mediated by the administration of a CD19×CD3 bispecific antibody to a human patient;
wherein said antibody is to be administered in accordance with a dosage regimen as defined in any one of the preceding disclosure.

Also, the present invention relates to a CD19×CD3 bispecific antibody
(i) administering a CD19×CD3 bispecific antibody to a human patient, or
(ii) treating malignant CD19 positive lymphocytes in a human patient; and/or
(iii) ameliorating or preventing an adverse effect mediated by the administration of a CD19×CD3 bispecific antibody to a human patient;
wherein said antibody is to be administered in accordance with a method as defined in any one of the preceding disclosure.

In a further aspect, the present invention concerns the use of a CD19×CD3 bispecific antibody for the preparation of a pharmaceutical composition to be used in a method as defined in any one of the methods described herein.

The pharmaceutical composition of the present invention may optionally comprise a pharmaceutical carrier. Examples of suitable pharmaceutical carriers are well known in the art and include phosphate buffered saline solutions, sterile solutions etc. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as chemotherapeutic agents as explained herein elsewhere.

In a further aspect, the present invention relates to a (pharmaceutical) kit or pharmaceutical package comprising the first dose and the second dose as defined herein.

In another embodiment, the present invention relates to a (pharmaceutical) kit or pharmaceutical package comprising the first dose and the second dose as defined herein as well as the third dose as defined in the context of the three-stage dosage regimen/method.

In another aspect, the (pharmaceutical) kit or pharmaceutical package comprises all three doses as defined herein in the context of the three-stage dosage regimen/method, i.e., the first, the second and the third dose.

Said first, second and third dose are thereby packaged together in one sealed pharmaceutical package or kit. It will be understood that the "first dose", the "second dose" and the "third dose" encompasses in this regard the respective number of single doses which will be used for a given period of time (either the first or the second period of time). This means for example that the "first dose" or "second dose" which is comprised in the pharmaceutical package or kit of the present invention comprises, for example, 7 daily doses which are separated. The number of packaged daily doses thereby reflects the intended period of time (X daily doses if said period of time is X days, Y daily doses if the period of time is Y days and so on). In these embodiments, the (pharmaceutical) kit or pharmaceutical package comprises the daily dosages in separate containers, in a single package.

Alternatively, it is also envisaged that the intended first dose and/or second dose and/or third dose is not separated into the respective number of daily doses but is contained, either in toto or in part, in one single container (for example an infusion bag), which comprises the required dose for either the first and/or the second period of time either in part (for example for 1 to 3 days) or in toto (i.e. for the first or second period of time). This means that one single container comprises, for example, 7 daily doses for the "first dose" which is to be used during the first period of time, and similarly for the second and third doses.

It will be understood that the (pharmaceutical) kit or pharmaceutical package of the present invention may also comprises more or less daily doses as required for the respective period of time (either separated or not). Alternatively, the (pharmaceutical) kit or pharmaceutical package is prepared such that it contains the required number of daily doses (either separated or not) for the first and second period of time as defined herein, i.e. the "first dose", the "second dose" and the "third dose" in one single package. Such a package is ideally sufficient for one complete treatment of a patient (including the first and the second period of time). Parts of the kit and package of the invention can be packaged individually in vials or bottles or in combination in containers or multicontainer units. The manufacture of the kits follows preferably standard procedures which are known to the person skilled in the art.

Furthermore, the invention relates to a pharmaceutical package or kit as described hereinbefore and written instructions for the sequential use thereof in accordance with the methods of the present invention. Said pharmaceutical package or kit may further comprise a label or imprint indicating that the contents can be used for treating malignant CD19 positive lymphocytes present in lymphoma or leukemia in a human patient; or for ameliorating or preventing an adverse effect mediated by the administration of a CD19×CD3 bispecific antibody to a patient.

It is also envisaged that the pharmaceutical package or kit of the present invention, further comprises means to administer the first and/or the second dose and/or third dose to a patient and/or buffers, vials, teflon bags or infusion bags which are normally used for the infusion of therapeutic agents. "Means" thereby includes one or more article(s) selected from the group consisting of a syringe, a hypodermic needle, a cannula, a catheter, an infusion bag for intravenous administration, intravenous vehicles, vials, buffers, stabilizers, written instructions which aid the skilled person in the preparation of the respective doses and infusions of the invention etc.

It is also envisaged that the pharmaceutical package or kit of the present invention further comprises a chemotherapeutic agent.

In a further aspect, the present invention provides for a pharmaceutical package or kit, wherein said first and/or said second dose is arranged such, that it is suitable for (prepared for) administration of a dosage regimen in accordance with a method of any one of the preceding disclosures.

THE FIGURES SHOW

FIG. 1: B cell counts from patient samples are stratified as predictor of risk of adverse effects in patients treated with a CD19×CD3 bispecific antibody.

FIG. 2: B cell counts of patient samples as a predictor in comparison to B:T cell ratios. A) and B) are results from two clinical studies treating patients with a CD19×CD3 bispecific antibody (A: trial 103-104, NHL; B: trial 103-202, ALL).

EXAMPLES

The following examples illustrate the invention. These examples should not be construed as to limit the scope of this invention. The examples are included for purposes of illustration and the present invention is limited only by the claims.

Example 1

Identification of a predictive factor for reversible neurological adverse events in a subset of non-Hodgkin lymphoma patients treated with CD19-specific BiTE antibody blinatumomab Blinatumomab is a CD19/CD3-bispecific antibody construct of the bispecific T cell engager (BiTE®) class showing as single agent a high rate and duration of responses in patients with relapsed non-Hodgkin lymphoma (NHL) and B-precursor acute lymphocytic leukemia (ALL). Blinatumomab has a favorable safety profile with exception of a subset of patients developing neurological adverse events (AEs) during the first days of treatment, such as confusion, speech impairment or cerebellar symptoms. Thus far, all relevant neurological AEs (11 out of 48 patients) were transient, fully reversible and resolved without sequelae within 3 to 72 hours after stop of infusion. In no case, pathological findings were seen upon cranial magnetic resonance imaging. Despite treatment discontinuation, 4 patients with neurological AEs have achieved an objective lymphoma remission. Analysis of cerebrospinal fluid (CSF) taken within hours after stop of infusion showed detectable levels of blinatumomab in the majority of affected patients, while in one patient without neurological symptoms no blinatumomab was detectable in CSF during infusion. Moreover, increased levels of albumin and T lymphocytes in CSF support a disturbance of the blood brain barrier (BBB) as a possible underlying event. Analyses of patient serum samples for angiopoetin-2 and S100β are ongoing to investigate whether levels of the endothelial stress and BBB integrity marker, respectively, correlate with neurological AEs. In a retrospective analysis of 39 NHL patients, a baseline B cell to T cell (B:T) ratio in peripheral blood at or below 1:10 was identified as the only predictive factor for the subsequent occurrence of neurological AEs. The predictive value was then prospectively confirmed in 8 additional patients. In conclusion, a simple measure to prospectively identify patients at risk of developing neurological AEs after onset of blinatumomab treatment has been identified. Mitigating measures are currently being tested in these high-risk patients in order to avoid discontinuation of treatment.

Example 2

Synopsis of observations (1) in patients treated with a CD19×CD3 bispecific antibody
Common Features of Early CNS Events
  First symptoms appear 12-48 h after start of MT103 infusion: Agitation, speech impairment, sometimes tremor, ataxia
  More severe symptoms leading to Infusion stop appear after 24-72 h: Confusion, disorientation, ataxia, aphasia, seizure
  After stop of MT103 infusion, complete resolution of CNS symptoms seen within 1-3 days; generally no sequelae
  Most CNS events fall into early activation and redistribution phase of polyclonal T cells
Features of CNS Events with Slow Onset
  Biased to cerebellar symptoms
  Occur at various time points during treatment, frequently at beginning of treatment or at step increase
  Tremor, mild speech impairment, mild writing impairment; can last for several days
Other CNS Events
  Additional symptoms observed without proven relationship to other CNS events: Headache, Fever, Nausea
MT103 Dose Response Relationship of CNS Events
  Dose response relationship of CNS events is evident; cut off is between dose level of 5 and 15 µg/m²/d Example 3

Synopsis of observations (2) in patients treated with a CD19×CD3 bispecific antibody
CNS Events Appear to be Predictable
  Correlation of CNS events with low B:T cell ratio (or low B cell count)
  B:T ratio of <1:10 identified as apparent cut off for development of CNS events
  No other biochemical or clinical parameters appear to correlate with CNS events
Cranial MRI of Patients with CNS Events Mostly without Pathological Findings CSF Analyses Suggest Opening of BBB and Neuroinflammatory Event
  Detectable levels of MT103 and increased levels of protein and serum albumin found in majority of affected patients suggest temporary breakdown of blood brain barrier (BBB)

No MT103 found in CSF of one patient free of CNS events

CSF analysis also shows in some affected patients increased counts of monocytes and T lymphocytes indicative of neuroinflammatory process Are CNS events reflecting gradual opening of BBB (agitation>confusion>aphasia, ataxia>seizure)?

Incidence of CNS Events May Correlate with Disease and/or Tumor Load

At 15 μg/m²/d, 3/8 NHL patients (37%) and only one of 1/11 ALL 'high risk' patients (9%) developed CNS events B-ALL patients routinely receive intrathecal chemotherapy (and i.v. high-dose methotrexate) likely reducing tumor cell load in CNS ("occult meningeosis neoplastica")

Example 4

Summary of CNS events in patients treated with a CD19× CD3 bispecific antibody

Summary of Clinically Relevant CNS Events in NHL Patients

| Patient # | Neurological Assessment | Disease | B:T cell ratio | Gender, Age | First or Additional Treatment | Dose in μg/m²/Day | Treatment Stop after Start | Complete Resolution, Time | Best Response |
|---|---|---|---|---|---|---|---|---|---|
| 105-005 | Confusion, communication disorder | FL | 1:23.9 | Female, 65 | First | 15 | 15 h | Yes, 24 h | SD |
| 102-004 | Organic Brain Syndrome | MCL | 1:757 | Male, 75 | First | 15 | 50 h | Yes, 34 h | n.d. |
| 102-006 | Generalized seizure (acidosis) | MZL | 1:1740 | Male, 59 | First | 30 | 48 h | Yes, 48 h | n.d. |
| 109-011 | Cerebellar Symptoms | MCL | 1:9.2 | Male, 73 | Restart | 60 | 48 h | Yes, 24 h | PR (first) |
| 109-012 | Encephalopathy | MCL | 1:19520 | Male, 55 | Additional | 60 | 24 h | Yes, 24 h | CR (first) |
| 102-007 | Seizure, aphasia | FL | 1:197 | Male, 61 | First | 90 | 48 h | Yes, 48 h | ?PR? |
| 109-023 | Encephalopathy | MCL | 1:368 | Male, 60 | First | 60 | 17 h | Yes, 56 h | n.d. |
| 109-025 | Encephalopathy | MCL | 1:873 | Male, 58 | First | 15 | 41 h | Yes, 48 h | n.d. |
| 108-004 | Speech Impairment Palsy Face and Arm | FL | 0:431 | Male, 66 | First | 60 | 624 h | Yes, 3 h | PR |
| 109-261 | Desorientation, Speech Impairment | MCL | 1:20 | Male, 42 | Additional | 60 | 30 h | Yes, 72 h | PR (first cycle) |

Example 5

Dose dependency of CNS events of patients treated with a CD19×CD3 bispecific antibody in Clinical Trials Dose Dependency of CNS Events in Ongoing NHL Trial
'High risk' patients defined by having low B:T cell ratio (<1:10)
Initial dose considered for classification in dose groups

| Dose | All | 'High Risk' | 'Low Risk' |
|---|---|---|---|
| ≤5 | 0/14 (0%) | 0/4+ (0%) | 0/10 (0%) |
| 15 | 3/16 (19%) | 3/8+ (38%) | 0/8 (0%) |
| 30 | 1/6 (17%) | 1/1 (100%) | 0/5 (0%) |
| 60 | 5/13 (38%) | 4/5 (80%) | 1*/8 (13%) |
| 90 | 2/3 (66%) | 1/1 (100%) | 1/2 (50%) |
| All | 11/52§ (21%) | 9/19 (47%) | 2/33 (6%) |

§>48 patients is due to additional treatments and re-starts of individual patients (resulting in conversion to 'high risk')
*Reached borderline B:T ratio after first treatment cycle
+Incl. patients with step-wise dose increase Example 6

A patient having an increased risk of potential adverse effects who received 15 μg/m²/d for 7 days and 60 μg/m²/d for 21 days showed no adverse effects (neurological reactions)

Patient 108-003
Female, 66 y
FL grade 2, IVB (FD: 09/2006)
Relevant medical history: anemia, thrombocytopenia, (pre-treatment 2× Zevalin and bone marrow infiltration by FL) elevation of gGT and AP, abuse of benzodiazepines, status after 2. aureaus sepsis with spondylodiscitis and abscesses
Prior lymphoma treatment:
6×R-CHOP 14, 8×R 09/2006-02/2007
R mono 05/07
1. Zevalin 11/07
2. Zevalin 01/08
According to initial B:T cell ratio (1:10.5) high-risk (cohort 15/60)

Jan. 5, 2009 Treatment start (15 μg/m²/24 h)
Fever, headache for 2 days—easily handled by oral paracetamol and novalgin
January 12th dose increase to 60 μg/m²/24 h
Again fever, headache—easily handled by oral paracetamol and novalgin
No neurological events
Well tolerated dose "step"
Suspected improvement of bone marrow function Example 7

A patient having an increased risk of potential adverse effects who received 5 μg/m²/d for 7 days and 60 μg/m²/d for 21 days showed mild adverse effects (neurological reactions)

MCL, male 42 y
B:T 1:12
Treatment start Jan. 19, 2009 with 5 micg/m2/d
Day 1: fever and chills, headache, no further problems Step: January 26th: after 6 h fever, strong headache
27 Jan. 2009: tiredness, nausea, vomiting, endoscopy without pathological findings), absolute arrhythmia with frequency up to 170/min→resolution within one day after substitution of potassium and digitoxin.
Cranial CT scan and CSF performed, CT: no pathological findings
CSF: slightly elevated protein 55 mg/dL, cells: 23 Zellen/micL, mainly monocytic cells and some activated lymphocytes
27 Jan. 2009 afternoon: mild tremor, apraxia, "slow mental state", evening: mild speech impairment (cerebellar?), slow improvement over the next two days 29 Jan. 2009 due to ongoing mild symptoms decision to give dexamethasone
Slow improvement of symptoms, complete resolution 31 Mar. 2009
During the further course of treatment: recurrent difficulties to play the guitar.
After 4 weeks treatment: −37%
After 8 weeks of treatment: PR/CRu Example 8

A patient having an increased risk of potential adverse effects who received a treatment regimen according to the present invention.
Patient 108-005
Male, 71 y, FL IIIB
B:T cell ratio: 57:1363 (low, 1:23.9)
First diagnosis: 1997
Multiple prior treatments: 12× Rituximab (mono), 6× Rituximab-Bendamustin, 6×R-CHOP, autologous SCT
Date of Blinatumomab start: 17 Oct. 2009
Treatment duration: 8 weeks
Well tolerated (no SAE)
No neurological adverse event
8 Week CT Scan: −65%=partial remission of the lymphoma Example 9

A further patient having an increased risk of potential adverse effects who received a treatment regimen according to the present invention.
Patient 109-031
Male, 60 y, Follicular Lymphoma IVAE
B:T cell ratio: 0:429 (low)
First diagnosis: 05/09
Prior treatments: Pre-phase w. Vincristin/Decortin, 6×R-CHOP
Blinatumomab treatment Start: 30 Nov. 2009
Treatment duration: 8 weeks
Well tolerated (flush symptoms at steps—responsive to steroids)
No neurological adverse event
Lymphoma—56% after 8 weeks (partial remission of the lymphoma)

The invention claimed is:

1. A method for treating a human patient suffering from malignant CD19-positive lymphoma or leukemia, wherein the patient is at risk for potential adverse effects resulting from treatment with a CD19×CD3 bispecific antibody comprising an amino acid sequence encoded by the nucleic acid sequence set forth in SEQ ID NO: 2 or the amino acid sequence set forth in SEQ ID NO: 1, the method comprising:
   (a) determining in the peripheral blood of the patient a ratio of B cells to T cells and total B cell count; and
   (b) identifying the patient at risk as comprising a ratio of B cells to T cells of about 1:8 or lower;
      (i) wherein a total B cell count of less than 40 B cells per microliter of peripheral blood is indicative of a higher risk for potential adverse effects for said patient; and
      (ii) wherein a total B cell count of 40 B cells or greater per microliter of peripheral blood is indicative of a lower risk of potential adverse effects for said patient,
   (c) administering the CD19×CD3 bispecific antibody
      (i) to the patient who is at higher risk in an incremental dosage schedule to reduce the possibility of potential adverse effects in the patient,
   wherein a first dose is administered for a first period of time and a second dose is consecutively administered for a second period of time,
   wherein said second dose is greater than said first dose, and
   wherein said second period of time exceeds said first period of time; or
      (ii) to the patient who is at lower risk in a constant dose for at least four weeks.

2. The method of claim 1, wherein the specific dosage schedule for said higher risk patient comprises:
   (a) administering a first dose of the CD19×CD3 bispecific antibody for a first period of time of 7 days; and consecutively
   (b) administering a second dose of said antibody for a second period of time that exceeds the first period of time; and optionally consecutively,
   (c) administering a third dose of said antibody for the first or second period of time or for a third period of time, wherein said second dose exceeds said first dose and said third dose exceeds said second dose.

3. The method of claim 1, wherein said adverse effect is characterized by a neurological reaction.

4. The method of claim 2, wherein:
   said second period of time exceeds said first period of time;
   said third period of time exceeds said first period of time and/or said second period of time;
   said first period of time exceeds 3 days;
   said first period of time is between 3 and 10 days, or is 7 days;

said second period of time exceeds 18 days; said second period of time is between 18 and 81 days, is 21 days, or is 49 days;

said first period of time is between 3 days and 10 days, and said second period of time is between 18 and 81 days; or said first period of time is 7 days and said second period of time is 21 days or is 49 days.

5. The method of claim 2, wherein
said first dose is between 1 and 15 µg/m²/d, or 5 or 15 µg/m²/d; or
said second dose is between 15 and 60 µg/m²/d, or is 60 µg/m²/d.

6. The method of claim 2, further comprising administering a third dose of said antibody for a third period of time after a first and second dose for a first and second period of time.

7. The method of claim 6, wherein
said third period of time exceeds said first and second period of time, and wherein said second dose exceeds said first dose;
said first period of time exceeds 3 days;
said first period of time is between 3 and 10 days, or is 7 days;
said second period of time exceeds 3 days;
said second period of time is between 3 and 10 days, or is 7 days;
said third period of time exceeds 8 days;
said third period of time is between 8 and 78 days, or is 14 days, or is 42 days;
said first period of time is between 3 and 10 days, and said second period of time is between 3 and 10 days, and said third period of time is between 8 and 78 days; or
said first period of time is 7 days, said second period of time is 7 days, and said third period of time is 14 days, or is 42 days.

8. The method of claim 6, wherein
said third dose exceeds said first and second dose;
said first dose is 5 µg/m²/d or is between 1 and 15 µg/m²/d, or wherein said first dose is between 2 and 29 µg/d, or is 9 or 10 µg/d;
said second dose is 15 µg/m²/d or is between 1 and 15 µg/m²/d, or wherein said second dose is between 2 and 29 µg/d, or is 28 or 29 µg/d; or said third dose is 60 µg/m²/d or is between 15 and 60 µg/m²/d, or wherein said third dose is between 28 and 116 µg/d, or is 112 µg/d.

9. The method of claim 1, wherein the lymphoma comprises indolent or aggressive B cell non-Hodgkin lymphoma (B NHL), mantle cell lymphoma (MCL) or chronic lymphatic leukemia (CLL).

10. The method of claim 1, wherein the leukemia comprises B-lineage acute lymphoblastic leukemia (ALL).

11. The method of claim 1, further comprising periodically determining the ratio of B cells to T cells and/or total B cell counts during administration of said antibody.

12. The method of claim 11, wherein the administering of the bispecific antibody may be adjusted based upon results of periodically determining the ratio of B cells to T cells and/or total B cell count to reduce the risk for potential adverse effects during the treatment.

13. The method of claim 1, wherein said second period of time exceeds 18 days.

14. The method of claim 13, wherein said second period of time is between 18 days and 81 days, or between 21 and 49 days.

15. The method of claim 13, wherein said first period of time is 7 days and said second period of time is 21 or 49 days.

16. The method of claim 1, wherein said first dose is between 1 and 15 µg/m²/d, or wherein said first dose is between 2 and 29 µg/d.

17. The method of claim 1, wherein said second dose is between 15 and 60 µg/m²/d, or wherein said second dose is between 28 and 116 µg/d.

18. The method of claim 1, wherein the method further comprises administering a third dose of said antibody for a third period of time after a first and second dose for a first and second period of time.

19. The method of claim 18, wherein said third period of time exceeds said first and second period of time, and wherein said second dose exceeds said first dose.

20. The method of claim 18, wherein said third dose exceeds said first and second dose.

* * * * *